US008883166B2

(12) United States Patent
Contorni et al.

(10) Patent No.: US 8,883,166 B2
(45) Date of Patent: Nov. 11, 2014

(54) COMBINATION VACCINES WITH WHOLE CELL PERTUSSIS ANTIGEN

(75) Inventors: Mario Contorni, Siena (IT); Donatella Mannucci, Siena (IT)

(73) Assignee: Novartis AG (CH)

( * ) Notice: Subject to any disclaimer, the term of this patent is extended or adjusted under 35 U.S.C. 154(b) by 1182 days.

(21) Appl. No.: 11/886,556

(22) PCT Filed: Mar. 16, 2006

(86) PCT No.: PCT/IB2006/001124
§ 371 (c)(1),
(2), (4) Date: Dec. 16, 2008

(87) PCT Pub. No.: WO2006/097851
PCT Pub. Date: Sep. 21, 2006

(65) Prior Publication Data
US 2009/0214586 A1    Aug. 27, 2009

(30) Foreign Application Priority Data

Mar. 17, 2005   (GB) .................................. 0505518.1

(51) Int. Cl.
| A61K 39/095 | (2006.01) |
| A61K 39/102 | (2006.01) |
| A61K 39/29 | (2006.01) |
| A61K 39/00 | (2006.01) |

(52) U.S. Cl.
CPC ............. *A61K 39/095* (2013.01); *A61K 39/292* (2013.01); *A61K 2039/6037* (2013.01); *A61K 39/102* (2013.01); *A61K 2039/521* (2013.01); *A61K 2039/627* (2013.01)
USPC .................................. 424/194.1; 424/196.11

(58) Field of Classification Search
CPC ........................... A61K 39/095; A61K 39/102
USPC ....................................................... 424/194.1
See application file for complete search history.

(56) References Cited

U.S. PATENT DOCUMENTS

| 4,356,170 A * | 10/1982 | Jennings et al. ........... 424/194.1 |
| 5,097,020 A * | 3/1992 | Anderson et al. ............. 530/403 |
| 5,955,079 A * | 9/1999 | Mond et al. ................. 424/193.1 |

(Continued)

FOREIGN PATENT DOCUMENTS

| EP | 1587537 | 10/2005 |
| EP | 1755662 | 2/2007 |

(Continued)

OTHER PUBLICATIONS

Constantino, Paolo et al, Size fractionation of bacterial capsular polysaccharides for their use in conjugate vaccines, Vaccine, vol. 17, 1999, pp. 1251-1263.*

(Continued)

*Primary Examiner* — Albert Navarro
*Assistant Examiner* — Ginny Portner
(74) *Attorney, Agent, or Firm* — Helen Lee; Otis Littlefield

(57) ABSTRACT

Vaccines have been studied that comprise (a) D-T-Pw-HepB-Hib antigens and (b) one or more meningococcal conjugate antigens. A number of improvements and variations of these vaccines have been discovered. The vaccines can be prepared extemporaneously at the time of use by mixing together two components: (a) a first component comprising D, T, wP and HBsAg antigens; and (b) a second component comprising a Hib conjugate and one or more meningococcal conjugates.

21 Claims, 4 Drawing Sheets

(56) References Cited

U.S. PATENT DOCUMENTS

| | | | |
|---|---|---|---|
| 6,248,334 B1* | 6/2001 | Lees et al. | 424/236.1 |
| 6,403,099 B1* | 6/2002 | Rappuoli et al. | 424/248.1 |
| 6,440,423 B1* | 8/2002 | Clements et al. | 424/236.1 |
| 6,756,040 B2* | 6/2004 | Peetermans et al. | 424/201.1 |
| 7,348,006 B2* | 3/2008 | Contorni et al. | 424/184.1 |
| 7,537,766 B2* | 5/2009 | Pavliak et al. | 424/184.1 |
| 8,007,818 B2* | 8/2011 | Garcon et al. | 424/256.1 |
| 2002/0054884 A1* | 5/2002 | Peetermans et al. | 424/196.11 |
| 2003/0022304 A1* | 1/2003 | Artois et al. | 435/69.1 |
| 2003/0113342 A1* | 6/2003 | Zhao et al. | 424/189.1 |
| 2003/0124139 A1* | 7/2003 | Esikova et al. | 424/185.1 |
| 2003/0180316 A1* | 9/2003 | Boutriau et al. | 424/190.1 |
| 2005/0025780 A1* | 2/2005 | Rubido et al. | 424/189.1 |
| 2005/0031646 A1* | 2/2005 | Capiau et al. | 424/203.1 |
| 2005/0106181 A1* | 5/2005 | Constantino | 424/238.1 |
| 2005/0118275 A1* | 6/2005 | O'Hagan | 424/490 |
| 2005/0220854 A1* | 10/2005 | Maa et al. | 424/449 |
| 2005/0266011 A1* | 12/2005 | Maa et al. | 424/184.1 |
| 2006/0127414 A1* | 6/2006 | Mayeresse et al. | 424/201.1 |
| 2007/0003566 A1* | 1/2007 | Rappuoli et al. | 424/186.1 |
| 2007/0116711 A1* | 5/2007 | Castado et al. | 424/190.1 |
| 2008/0199487 A1* | 8/2008 | Galli | 424/193.1 |
| 2008/0254057 A1* | 10/2008 | Costantino | 424/197.11 |
| 2008/0305127 A1* | 12/2008 | Poolman | 424/194.1 |
| 2009/0208526 A1* | 8/2009 | Contorni | 424/196.11 |
| 2010/0092509 A1* | 4/2010 | Costantino et al. | 424/197.11 |
| 2012/0207780 A1* | 8/2012 | Boutriau et al. | 424/196.11 |
| 2012/0258126 A1* | 10/2012 | Scholler et al. | 424/186.1 |
| 2012/0321660 A1* | 12/2012 | Biemans et al. | 424/197.11 |
| 2013/0071422 A1* | 3/2013 | Pallaoro et al. | 424/189.1 |
| 2013/0171188 A1* | 7/2013 | Biemans et al. | 424/197.11 |
| 2014/0234368 A1* | 8/2014 | Costantino et al. | 424/197.11 |

FOREIGN PATENT DOCUMENTS

| | | | |
|---|---|---|---|
| EP | 1835939 | | 4/2010 |
| WO | 9324148 | * 12/1993 | A61K 39/295 |
| WO | WO-93/24148 A1 | 12/1993 | |
| WO | WO-97/00697 A1 | 1/1997 | |
| WO | 99/13906 | * 3/1999 | A61K 39/295 |
| WO | 02/00249 | * 1/2002 | A61K 39/00 |
| WO | WO 02/00249 | 1/2002 | |
| WO | WO-02/58737 | 8/2002 | |
| WO | WO 02/080965 | 10/2002 | |
| WO | 03/007985 | * 1/2003 | A61K 39/02 |
| WO | WO-03/007985 | 1/2003 | |
| WO | 03/009869 | * 2/2003 | A61K 39/39 |
| WO | 03009869 | * 2/2003 | A61K 39/39 |
| WO | 2004/067030 A2 | 8/2004 | |
| WO | WO-2004/067030 | 8/2004 | |
| WO | WO-2004/110480 A2 | 12/2004 | |
| WO | WO-2005/000345 | 1/2005 | |
| WO | WO 2005/020964 | 3/2005 | |
| WO | WO 2005/032583 | 4/2005 | |
| WO | 2005089794 | * 9/2005 | A61K 39/12 |
| WO | WO-2006/097851 A2 | 9/2006 | |

OTHER PUBLICATIONS

Constantino, 1999, Vaccine, vol. 17, pp. 1251-1263.*

Abstract Book, (Sep. 5-10, 2004). "Abstracts of the 14th International Pathogenic *Neisseria* Conference," The 14th International Pathogenic *Neisseria* Conference, Milwaukee, Wisconsin, USA, pp. 1-168.

Amir, J et al. (1997). "Immunogenicity and safety of a Liquid Combination of DT-PRP-T vs Lyophilized PRP-T Reconstituted with DTP," *Vaccine* 15(2):149-154.

Avendano et al. (Dec. 12, 1993). "*Haemophilus influenzae* type b polysaccharide-tetanus protein conjugate vaccine does not depress serologic responses to diphtheria, tetanus or pertussis antigens when coadministered in the same syringe with diphtheria-tetanus-pertussis vaccine at two, four, and six months of age," *Pediatr Infect Dis J* 12(8):638-643.

Aventis Pasteur SA (Jul. 1998), "Act-HIB® Product Information," 11 pages.

Barington, T. et al. (1993) "Non-epitope-specific suppression of the antibody response to *Haemophilus influenzae* type b conjugate vaccines by preimmunization with vaccine components," *Infection and Immunity* 61 (2):432-438.

Barington, T. et al. (1994) "Opposite effects of actively and passively acquired immunity to the carrier on responses of human infants to a *Haemophilus* influenzae type b conjugate vaccine," *Infection and Immunity* 62(1):9-14.

Bauminger et al. (1980) "The use of Carbodiimides in the Preparation of Immunizing Conjugates" *Methods in Enzymology* 70:151-159.

Becker, R. S. (1993) "Conjugate vaccines: practice and theory," *Springer Semin. Immunopathol.* 15:217-226.

Berry et al. (Jul. 2002). "Effect of O Acetylation of *Neisseria meningitides* Serogroup A Capsular Polysaccharide on Development of Functional Immune Responses," *Infection and Immunity* 70(7):3707-3713.

Chu et al. (Apr. 1983). "Further Studies on the Immunogenicity of *Haemophilus influenzae* Type b and Pneumococcal Type 6A Polysaccharide-Protein Conjugates," *Infection and Immunity* 40(1):245-256.

Decker et al. (2003). "Chapter 29: Combination vaccines" in *Vaccines*. Plotkin (ed.) Elsevier, p. 825-861.

Gatchalian et al. (Dec. 12, 2008). "The development of a new heptavalent diphtheria-tetnaus whole cell pertussis—hepatitis B-*Haemophilus influenzae* b—*Neosseria meningitidis* serogroups A and C vaccine: a randomised dose-ranging trial of the conjugate vaccine components." *Int J Infectious Dis* 12:278-288.

Gatchalian, S et al. (Sep. 5, 2004), "Antibody persistence and immune meory in 10-month old infants primed with a heptavalent DTPw-HB/HibMenAC vaccines at 6, 10 and 14 weeks of age" Poster presented at IPNC USA.

Gatchalian, S et al. (Sep. 5, 2004), "Immunogenicity and safety of 3 doses of a new heptavalent DTPw-HBV/HIB-MenAC vaccine administered to infants at 6, 10 and 14 weeks of age" poster presented at IPNC.

Grabenstein, (Dec. 12, 2002). "ImmunoFacts: vaccines and Immunogenic Drugs" Elsevier, p. 159-169.

Granoff et al. (2003). "Chapter 34: Meningococcal vaccines" in *Vaccines*. Plotkin (ed.) Elsevier, p. 959-987.

Knezevic et al. (Apr. 2002), "Thiomersal in vaccines: a regulatory perspective WHO Consultation" *Vaccine* 22:1836-1841.

Komatsu et al. (2002). "Influence of Temperature on the Efficiency of 2-Phenoxyethanol as a Preservative for Adsorbed Diptheria-Purified Pertussis-Tetanus Combined Vaccine" *Journal of Health Science* 48(1):89-92.

Opposition to EP1858551 B1 filed on Feb. 4, 2011, by GlaxoSmithKline, 30 pages.

Opposition to EP1858551 B1 filed on Feb. 4, 2011, by Sanofi Pasteur, Inc., 30 pages.

Plotkin (Ed.) (2003). *Vaccines*, Fourth Edition. Elsevier.

Plotkin, S. A. and Mortimer, E. A., (eds), (1994) *Vaccines* (second edition), W.B. Saunders Company, p. 358; 365-366.

Romero et al. (Oct. 1994). "Current Status of Meningococcal Group B Vaccine Candidates Capsular or Noncapsular?" *Clinical Microbiology Reviews* 7(4):559-575.

Sanofi Pasteur (Nov. 2009), "Act-HIB® Product Information," 10 pages.

Sanofi Pasteur Inc. (Dec. 2005), "Tripedia® Product Information", 13 pages.

Schneerson, (May 1986). "Quantitative and Qualitative analyses of serum antibodies elicited in adults by *Haemophilus influenzae* Type b and Pneumococcus Type 6A capsular polysaccharide-tetanus toxoid conjugates." *Infection and Immunity* 52(2):519-528.

Siber, G. R. et al. (1995) "Development of a guinea pig model to assess immunogenicity of *Haemophilus influenzae* type b capsular polysaccharide conjugate vaccines," *Vaccine* 13(6):525-531.

Tritanrix™ HepB (2009)"Summary of Product Characteristics," published as Annex I to the EPAR (European Public Assessment Report), Product Information for Tritanrix™ HepB by the EMEA, 26 pages.

(56) References Cited

OTHER PUBLICATIONS

Van der Meeren (1994). "Phospholipid Composition of r-DNA Hepatitis B Surface Antigens," *International Journal of Pharmaceuticals* 106:89-92.

Vanderlandschoot, P. et al. (2003) "*Saccharomyces cerevisiae*-derived HBsAg preparations differ in their attachment to monocytes, immune-suppressive potential, and T-cell immunogenicity," *Journal of Medical Virology* 70: 513-519.

Watemberg et al. (Oct. 1991). "Safety and Immunogenicity of *Haemophilus* Type b-Tetanus Protein Conjugate Vaccine, Mixed in the Same Syringe with Diphtheria-Tetanus-Pertussis Vaccine in Young Infants" *Pediaric Infectious Disaeses Journal* 10(10):758-761.

Wenger et al. (2003). "Chapter 14: *Haemophilus* influenzae Vaccine" in Vaccines. Plotkin (ed.) Elsevier, p. 229-267.

Wikipedia (2011). "Thiomersal," accessed on Jan. 14, 2011, online at: 1 page.

Jodar, L., et al. "Scientific challenges for the quality control and production of group C meningococcal conjugate vaccines," Vaccine, 22: 1047-1053 (2004).

Ho, M., et al. "Physico-chemical and immunological examination of the thermal stability of tetanus toxoid conjugate vaccines," Vaccine, 20: 3509-3522 (2002).

Redhead, K., et al. "Combination of DTP and *Haemophilus influenzae* type b conjugate vaccines can affect laboratory evaluation of potency . . . " Biologicals, 22: 339-345 (1994).

Halperin, S., et al. "Simultaneous administration of meningococcal C conjugate vaccine and diphtheria-tetanus-acellular pertussis . . . " Clin Invest Med, 25(6): 243-251 (2002).

Mallet, E., et al. "A liquid hexavalent combined vaccine against diphtheria, tetanus, pertussis, poliomyelitis, *Haemophilus influenzae* type B . . . " Vaccine, 22: 1343-1357 (2004).

GB Patent Application No. 0505518.1, filed Mar. 17, 2005, by Chiron SRL. 54 pages.

Burrage et al. (2002), "Effect of vaccination with carrier protein on response to meningococcal C conjugate vaccines and value of different immunoassays as predictors of protection," Infect Immun. 70(9):4946-54.

Campbell et al. (2002), "Safety, reactogenicity, and immunogenicity of a tetravalent meningococcal polysaccharide-diphtheria toxoid conjugate vaccine given to healthy adults," J Infect Dis. 186(12):1848-51.

Lamb et al. (2000), "Capillary electrophoretic analysis of meningococcal polysaccharide-diphtheria toxoid conjugate vaccines ," Dev Biol (Basel). 103:251-8.

Declarations of Dominique Botriau and of Isabel De Vleeschauwer, submitted on Jan. 26, 2012, by GlaxoSmithKline Biologicals SA., in Opposition to EP1858551 B1, filed on Feb. 4, 2011. 56 pages.

Written Submissions submitted on Jul. 13, 2012, by GlaxoSmithKline Biologicals SA. 41 pages.

Declaration of Florence Wauters, dated Jul. 16, 2012, submitted by GlaxoSmithKline Biologicals SA., in Opposition to EP1858551 B1, filed on Feb. 4, 2011. 3 pages.

Interlocutory Decision in Opposition Proceedings in European Patent Application No. 06727568.5; Feb. 6, 2013.

* cited by examiner

FIGURE 1
FIGURE 1A
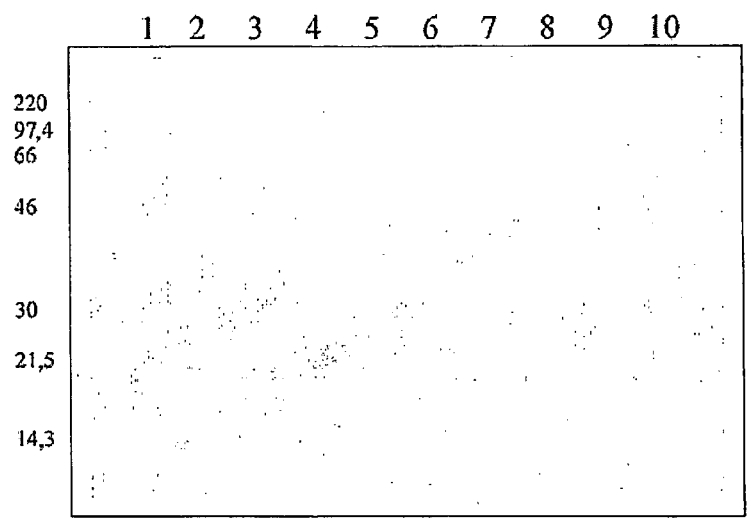
FIGURE 1B
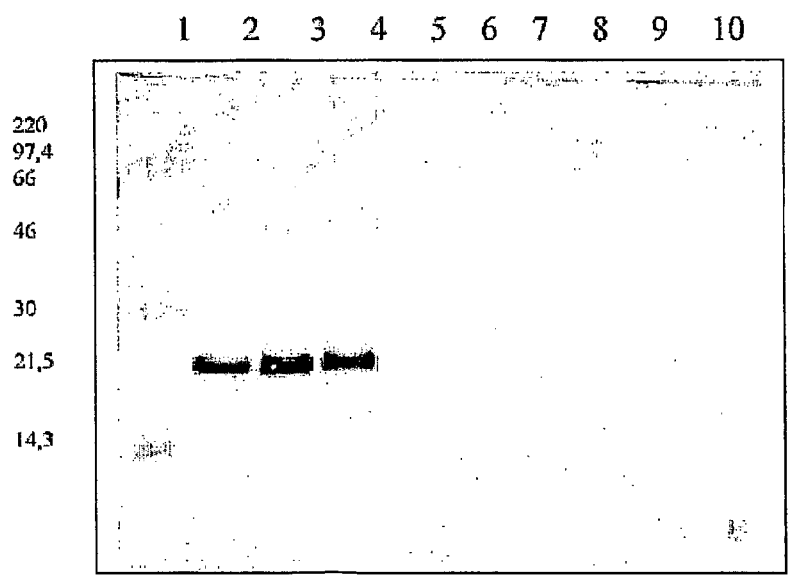

FIGURE 2
FIGURE 2A
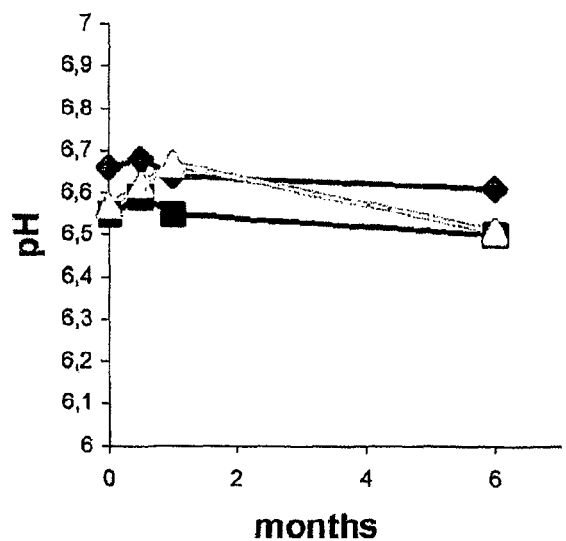
FIGURE 2B
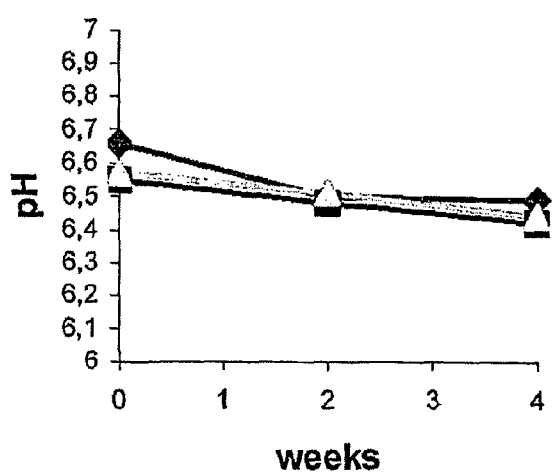

FIGURE 3
FIGURE 3A
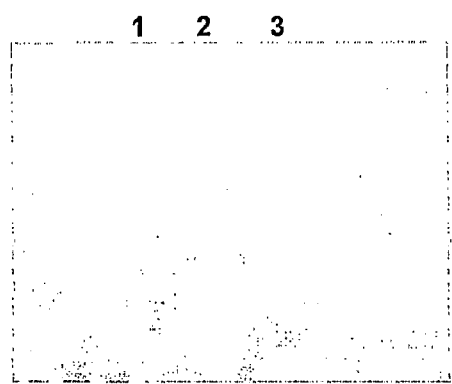
FIGURE 3B
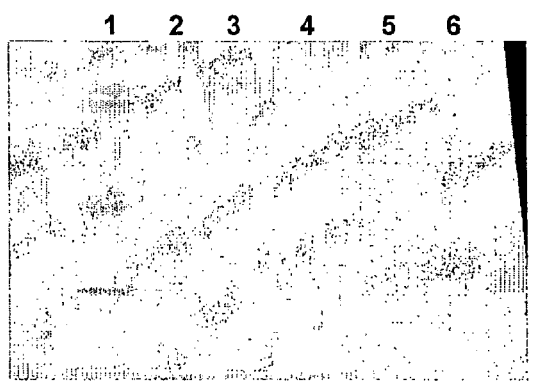

COMBINATION VACCINES WITH WHOLE CELL PERTUSSIS ANTIGEN

RELATED APPLICATIONS

This application is the U.S. National Phase of International Application No. PCT/IB2006/001124, filed Mar. 16, 2006 and published in English, which claims the benefit of Great Britain Application No. 0505518.1, filed Mar. 17, 2005. The teachings of the above applications are incorporated herein in their entirety by reference.

All documents cited herein are incorporated by reference in their entirety.

TECHNICAL FIELD

This invention is in the field of combination vaccines, that is vaccines containing a mixture of immunogens from more than one pathogen, such that administration of the vaccine can simultaneously immunize a subject against more than one pathogen.

BACKGROUND ART

Combination vaccines offer patients the advantage of receiving a reduced number of injections, which leads to the clinical advantage of increased compliance (e.g. see chapter 29 of reference 1).

Six pathogens of particular concern, particularly in children, are *Corynebacterium diphtheriae* (the cause of diphtheria), *Clostridium tetani* (the cause of tetanus/lockjaw), *Bordetella pertussis* (whooping cough), hepatitis B virus ('HepB', viral hepatitis), *Haemophilus influenzae* type b ('Hib', a cause of bacterial meningitis and pneumonia) and *Neisseria meningitidis* (meningococcal meningitis and septicaemia).

Vaccines against each of these pathogens are known, and a pentavalent vaccine including all five of the 'D', 'T', 'P', 'HepB', and 'Hib' components for simultaneous combined administration is marketed by GlaxoSmithKline under the name TRITANRIX-HepB/Hib. The 'P' component in this pentavalent vaccine is based on whole cell pertussis ('Pw') antigen. The DTP and HepB components of this vaccine are in a combined solution within a vial (and this tetravalent DTPw-HepB combination is sold separately as the 'TRITANRIX-HepB' product), but the Hib component is freeze-dried and contained in a separate vial. The DTPw-HepB solution is used to reconstitute the Hib component at the time of use, extemporaneously forming the pentavalent vaccine in the vial.

TRITANRIX-HepB/Hib does not protect against meningococcal infection.

Example 3 of reference 2 discloses the results of human clinical trials in which the tetravalent TRITANRIX-HepB product was extemporaneously mixed with conjugated capsular saccharides from Hib and from serogroups A and C of meningococcus ('MenA' and 'MenC'). The authors report that this heptavalent mixture induced a good immune response against each antigen and was well tolerated by infants. Full details of the Hib, MenA and MenC components are not given. Similar information is reported in references 3 and 4.

It is an object of the invention to provide further and improved combination vaccines for protecting against all six of *Corynebacterium diphtheriae*, *Clostridium tetani*, *Bordetella pertussis*, hepatitis B virus, *Haemophilus influenzae* type b and *Neisseria meningitidis*.

SUMMARY OF THE INVENTION

The invention is based on studies of vaccine that comprise D-T-Pw-HepB-Hib antigens (as in the TRITANRIX-HepB/Hib product) and also comprise one or more meningococcal conjugate antigens.

A number of improvements and variations of these vaccines have been discovered, and these are the topic of the invention.

Vaccines of the invention comprise:
(i) a diphtheria toxoid, 'D';
(ii) a tetanus toxoid, 'T';
(iii) a cellular pertussis antigen, 'wP';
(iv) a hepatitis B virus surface antigen, 'HBsAg';
(v) a *Haemophilus influenzae* type b capsular saccharide conjugated to a carrier protein;
(vi) at least one *Neisseria meningitidis* capsular saccharide conjugated to a carrier protein.

The meningococcal saccharide(s) can be from one or more of serogroups A, C, W135 and Y. Common nomenclature refers to these four serogroups as 'MenA', 'MenC', 'MenW135' and 'MenY'. Conjugate antigens are generally referred to herein as 'MenA-X' etc., where 'X' represents the conjugate's carrier protein. Conjugates with specific carrier proteins are then referred to as 'MenA-CRM' or 'MenC-D', etc.

Preferred vaccines contain meningococcal conjugates for at least serogroup C, and preferably for both serogroup A and C. Thus preferred vaccines are hexavalent (D-T-Pw-HBsAg-Hib-MenC) or heptavalent (D-T-Pw-HBsAg-Hib-MenA-MenC).

In addition to antigens (i) to (vi) listed above, further antigens may also be present e.g. to given an 8-valent, 9-valent, 10-valent, etc. vaccine.

Vaccines of the invention can be prepared in liquid format (i.e. where all antigens are in aqueous solution or suspension) during manufacture, or they can be prepared extemporaneously at the time of use by mixing together two components: (a) a first component comprising D, T, wP and HBsAg antigens; and (b) a second component comprising Hib and meningococcal conjugates. The two components are preferably in separate containers (e.g. vials and/or syringes), and the invention provides a kit comprising components (a) and (b). The contents of the first container are preferably aqueous, and the contents of the second container are preferably lyophilised, such that vaccines of the invention can be prepared by reconstituting the lyophilised component with the aqueous D-T-wP-HBsAg component.

(1) Weight Ratio of the Hib Conjugate

Hib conjugates are well known, but they come in various forms. For instance, Table 14-7 of reference 1 gives the characteristics of four different Hib conjugates. This table reports that the saccharide:carrier weight ratio varies between 1.4:1 in 'PRP-D' (excess saccharide) to 0.06:1 in 'PRP-OMP' (excess protein). All of these conjugates have been used in combination vaccines, but one aspect of the invention has selected a specific weight ratio range for use in combination vaccines that include meningococcal conjugates.

The weight ratio of carrier protein to saccharide in Hib conjugates has been reported to play an important role in the efficacy of combination vaccines. According to reference 5, in combination vaccines where the carrier protein is present also as an antigen (e.g. where tetanus toxoid is used both as a carrier and as an antigen, as in the present invention) then a Hib conjugate should have a saccharide:carrier weight ratio of between 1:0.3 and 1:2.

In contrast, according to the present invention, the weight ratio of saccharide to carrier can be beyond this range, and is between the range of 1:2 and 1:4. Hib conjugates in this range show excellent immunogenicity when combined with meningococcal conjugates in combination pediatric vaccines and do not duffer from any immune interference, even though the carrier protein is also present as free antigen (e.g. where the carrier protein is tetanus toxoid or diphtheria toxoid). Indeed, the extra carrier protein can contribute to immunity e.g. against tetanus or diphtheria.

Thus the invention provides a combination vaccine comprising (i) a diphtheria toxoid, (ii) a tetanus toxoid, (iii) a cellular pertussis antigen, (iv) a hepatitis B virus surface antigen, (v) a *Haemophilus influenzae* type b capsular saccharide conjugated to a carrier protein, (vi) at least one *Neisseria meningitidis* capsular saccharide conjugated to a carrier protein, characterised in that the *H. influenzae* conjugate has a weight excess of carrier to saccharide, wherein the weight ratio of carrier to saccharide is between 2:1 and 4:1.

The invention also provides a process for preparing a combination vaccine that comprises (i) a diphtheria toxoid ('D'), (ii) a tetanus toxoid ('T'), (iii) cellular pertussis antigen ('Pw'), (iv) a hepatitis B virus surface antigen ('HBsAg'), (v) a *Haemophilus influenzae* type b capsular saccharide conjugated to a carrier protein, (vi) at least one *Neisseria meningitidis* capsular saccharide conjugated to a carrier protein, characterised in that the process comprises the steps of: (a) combining a trivalent D-T-Pw component with a monovalent HBsAg component, to give a tetravalent D-T-Pw-HBsAg component; (b) combining the *H. influenzae* and *N. meningitidis* conjugates to give a mixed conjugate component, wherein the *H. influenzae* conjugate has a weight excess of carrier to saccharide with a weight ratio of carrier to saccharide of between 2:1 and 4:1; and (c) mixing the D-T-Pw-HBsAg component with the conjugate component, to give the combination vaccine.

The Hib conjugate has a weight excess of carrier protein. The weight ratio is between 2:1 and 4:1, and is preferably between 2.5:1 and 3.5:1. A weight ratio between 2.8:1 and 3.2:1 can be used, and a weight ratio of about 3:1 is preferred. At a typical dose of 10 μg (measured as saccharide), therefore, a composition of the invention will include between 20-40 μg of carrier, preferably about 30 μg. This ratio is in direct contrast to the teaching of reference 5.

The carrier protein for the Hib conjugate is preferably a tetanus toxoid, and so, for 10 μg of Hib saccharide, the composition can include 20-40 μg of tetanus toxoid from the Hib conjugate, plus further tetanus toxoid as the 'T' antigen for protecting against *C. tetani* infection.

Preferred compositions and processes use a meningococcal conjugate from serogroup C. More preferred compositions and processes use separate meningococcal conjugates from both of serogroups A and C. These are preferably conjugated to a *H. influenzae* protein D carrier, but they may also be conjugated to a tetanus toxoid carrier, a diphtheria toxoid carrier or a CRM197 carrier.

(2) Carrier/Saccharide Linkage in the Hib Conjugate

As shown in Table 14-7 of reference 1, various different linkage chemistries have been used for producing Hib conjugates. Some conjugates are formed by activating the saccharide, some by activating the carrier, and some by activating both. For saccharide activation, periodiate and cyanoborohydrate are used in the 'HbOC' product, and ADH, CNB and carbodiimide HCl are used in the 'PRP-T' product. All of these conjugates have been used in combination vaccines, but one aspect of the invention has selected a specific type of linkage for use in combination vaccines that include meningococcal conjugates.

According to the present invention, the polysaccharide can first be activated using cyanogen bromide, then coupled to an adipic acid linker, and this linker-saccharide entity is then reacted with a carrier protein, and in particular with a tetanus toxoid carrier protein.

The first step involves cyanylation of a free —OH group on the Hib saccharide, illustrated as follows:

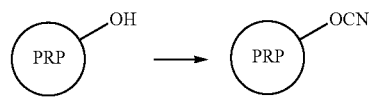

This reaction is achieved using cyanogen bromide (CNBr). Briefly, CNBr is reacted with the saccharide under acidic conditions (typically pH 10 to 12). At this high pH, cyanate esters are formed with the hydroxyl groups of the saccharide. The high pH ionises the hydroxyl group to allow nucleophilic attack of the hydroxyl ion on the cyanate ion. Because of the high pH, various side reactions can occur, but only the cyanate ester formation is the topic of the invention.

The cyanate ester is reacted with a bifunctional reagent (heterobifunctional or, preferably, homobifunctional) in order to provide a spacer for linking to the carrier. According to the invention, an adipic hydrazide spacer can be used. This can conveniently be achieved by using adipic acid dihydrazide (AADH):

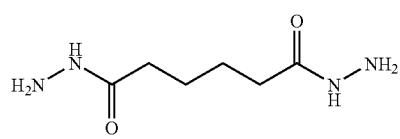 [SMILES: NNC(=O)CCCCC(=O)NN]

The mechanism of the AADH reaction with a cyanate ester (to form an imidocarbamate linkage) can be illustrated as:

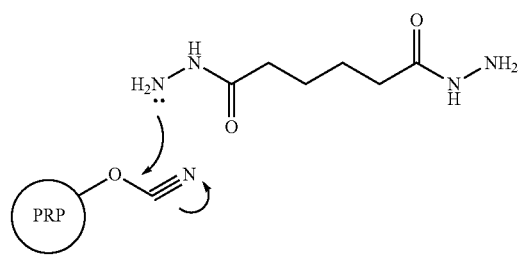

The activated saccharide is then reacted with a tetanus toxoid carrier in the presence of EDAC (1-ethyl-3-(3-dimethylaminopropyl)carbodiimide):

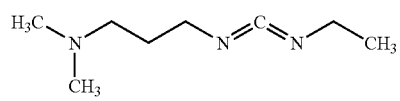

EDAC will typically be used in the form of its hydrochloride salt:

EDAC permits the carboxyl group at the free end of the adipic acid linker to react with the carrier protein (typically with a free —SH, —NH₂ or —OH on an amino acid side chain), to form a conjugate that can be illustrated as follows, where —X— is —S—, —O— or —NH—, originating from the carrier;

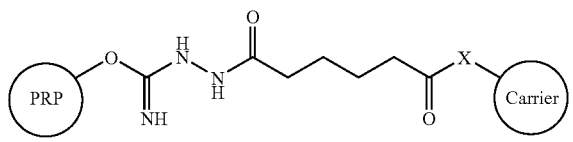

Under aqueous conditions the C=NH can convert to C=O, to give a carbamate:

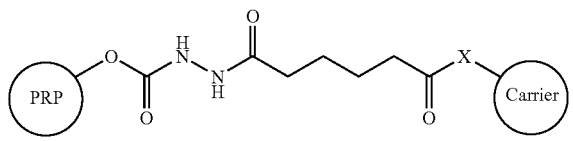

Thus the invention provides a combination vaccine comprising (i) a diphtheria toxoid, (ii) a tetanus toxoid, (iii) cellular pertussis antigen, (iv) a hepatitis B virus surface antigen, (v) a *Haemophilus influenzae* type b capsular saccharide conjugated to a carrier protein, and (vi) at least one *Neisseria meningitidis* capsular saccharide conjugated to a carrier protein, characterised in that the *H. influenzae* conjugate is obtainable by a process comprising the steps of: (a) activating a *Haemophilus influenzae* type b capsular saccharide with cyanogen bromide, to give a cyanate ester; (b) adding an adipic hydrazide spacer to the cyanate ester, to give an activated saccharide; and (c) coupling the activated saccharide to a carrier protein by carbodiimide condensation.

The invention also provides a combination vaccine comprising (i) a diphtheria toxoid, (ii) a tetanus toxoid, (iii) cellular pertussis antigen, (iv) a hepatitis B virus surface antigen, (v) a *Haemophilus influenzae* type b capsular saccharide conjugated to a carrier protein, (vi) at least one *Neisseria meningitidis* capsular saccharide conjugated to a carrier protein, characterised in that the *H. influenzae* conjugate of (v) includes a linker with one of the following two structures:

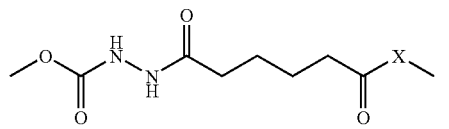

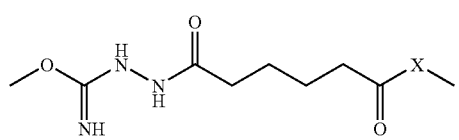

where —X— is selected from the group consisting of: —O—, —S— or —NH—. The carbamate is preferred.

The carrier protein for the Hib conjugate is preferably a tetanus toxoid.

Preferred compositions and processes use a meningococcal conjugate from serogroup C, and more preferred compositions and processes use separate meningococcal conjugates from both of serogroups A and C. These are preferably conjugated to a *H. influenzae* protein D carrier.

A mixture of Hib, MenA and MenC conjugates be used either for mixing with other vaccines or as a vaccine on its own. Thus the invention also provides a conjugate mixture comprising (i) a *Haemophilus influenzae* type b capsular saccharide conjugated to a carrier protein, (ii) *Neisseria meningitides* serogroup A capsular saccharide conjugated to a carrier protein, and (iii) *Neisseria meningitidis* serogroup C capsular saccharide conjugated to a carrier protein, characterised in that the *H. influenzae* conjugate is obtainable by a process comprising the steps of: (a) activating a *Haemophilus influenzae* type b capsular saccharide with cyanogen bromide, to give a cyanate ester; (b) adding an adipic hydrazide spacer to the cyanate ester, to give an activated saccharide; and (c) coupling the activated saccharide to a carrier protein by carbodiimide condensation.

The invention also provides a conjugate mixture comprising (i) *Haemophilus influenzae* type b capsular saccharide conjugated to a carrier protein, (ii) *Neisseria meningitidis* serogroup A capsular saccharide conjugated to a carrier protein, and (iii) *Neisseria meningitidis* serogroup C capsular saccharide conjugated to a carrier protein, characterised in that the *H. influenzae* conjugate of (i) includes a linker with one of the following two structures:

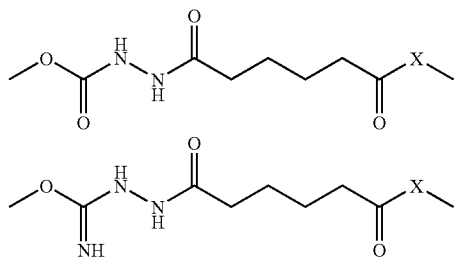

where —X— is selected from the group consisting of: —O—, —S or —NH—. The carbamate is preferred.

(3) Direct Carrier-Saccharide Linkage in the Meningococcal Conjugates

The Hib conjugate described above is linked to the carrier protein by a spacer. In contrast, it is preferred to use direct linkage in the meningococcal conjugates. Direct linkage has been found to be particularly suitable for meningococcal conjugates, especially where protein D is used as the carrier and where the Hib conjugate does not use direct linkage (to avoid the linkers from crossing any possible threshold at which they may become immunogenic).

In a direct linkage situation, a —OH group in the meningococcal saccharide is first cyanylated (e.g. as described above) to give a cyanate ester. The —OCN group is then used to link directly to a side chain in the carrier, such as a free —NH₂ group, a free —SH group or a free —OH group. Linkage to a free —NH₂ in a lysine side chain is preferred.

The mechanism of direct linkage can be illustrated as follows:

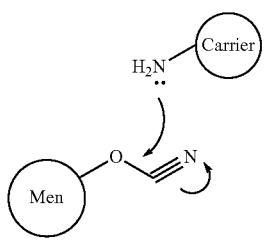

and the conjugated product of this reaction can be illustrated as follows:

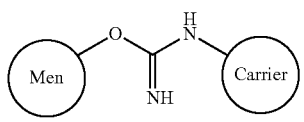

Under aqueous conditions the C=NH can be converted to C=O, to give a carbamate:

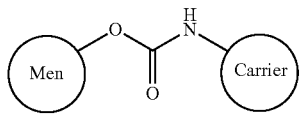

Rather than using cyanogen bromide as the cyanylating agent, the cyanylation reaction is preferably achieved using an organic cyanylating reagent, such as a 1-cyano-4-(dimethylamino)-pyridinium reagent ('CDAP'). The organic cyanylating reagent can be selected from the group consisting of 1-cyano-4-(dimethylamino)-pyridinium tetrafluoroborate, p-nitrophenylcyanate ('pNPC'), and N-cyanotriethyl-ammonium tetrafluoroborate ('CTEA'). Using these reagents means that the activation reaction can be carried out at neutral pH, which can help to retain the stability and integrity of the polysaccharide. In particular, it can help to retain —OAc groups (see below). In preferred methods, the cyanylating reagent is used at pH 6-8 in a non-nucleophilic buffer e.g. in saline, HEPES, phosphate, water and some organic solvents [6]. The CDAP can be dissolved in acetonitrile and added to an aqueous saccharide solution. After conjugation, the reaction can be quenched by the addition of glycine, which blocks any unreacted cyanate groups.

Concentrating on the meningococcal serogroup A conjugate, the invention provides a combination vaccine comprising (i) a diphtheria toxoid, (ii) a tetanus toxoid, (iii) cellular pertussis antigen, (iv) a hepatitis B virus surface antigen, (v) a *Haemophilus influenzae* type b capsular saccharide conjugated to a carrier protein, and (vi) *Neisseria meningitidis* serogroup A capsular saccharide conjugated to a carrier protein, characterised in that the serogroup A conjugate is obtainable by a process comprising the steps of: (a) cyanylating a serogroup A capsular saccharide to give a cyanate ester; and (b) coupling the cyanate ester directly to a protein carrier. The vaccine may also include (vii) *Neisseria meningitidis* serogroup C capsular saccharide conjugated to a carrier protein.

The invention also provides a process for preparing a conjugate mixture comprising (i) *Haemophilus influenzae* type b capsular saccharide conjugated to a carrier protein, (ii) *Neisseria meningitidis* serogroup A capsular saccharide conjugated to a carrier protein, and (iii) *Neisseria meningitidis* serogroup C capsular saccharide conjugated to a carrier protein, characterised in that the serogroup A conjugate is produced by a process comprising the steps of: (a) cyanylating a serogroup A capsular saccharide to give a cyanate ester; and (b) coupling the cyanate ester directly to a carrier protein.

Turning to the meningococcal serogroup C conjugate, the invention provides a combination vaccine comprising (i) a diphtheria toxoid, (ii) a tetanus toxoid, (iii) cellular pertussis antigen, (iv) a hepatitis B virus surface antigen, (v) a *Haemophilus influenzae* type b capsular saccharide conjugated to a carrier protein, and (vi) *Neisseria meningitidis* serogroup C capsular saccharide conjugated to a carrier protein, characterised in that the serogroup C conjugate is obtainable by a process comprising the steps of: (a) cyanylating a serogroup C capsular saccharide to give a cyanate ester; and (b) coupling the cyanate ester directly to a carrier protein. The vaccine may also include (vii) *Neisseria meningitidis* serogroup A capsular saccharide conjugated to a carrier protein.

The invention also provides a process for preparing a conjugate mixture comprising (i) *Haemophilus influenzae* type b capsular saccharide conjugated to a carrier protein, (ii)*Neisseria meningitidis* serogroup A capsular saccharide conjugated to a carrier protein, and (iii) *Neisseria meningitidis* serogroup C capsular saccharide conjugated to a carrier protein, characterised in that the serogroup C conjugate is produced by a process comprising the steps of: (a) cyanylating a serogroup C capsular saccharide to give a cyanate ester; and (b) coupling the cyanate ester directly to a carrier protein.

The invention also provides vaccines and processes in which both serogroup A and serogroup C conjugates are prepared in this manner and are then combined. A Hib conjugate can also be added, to give a conjugate mixture comprising all three of Hib, MenA and MenC.

(4) O-Acetylation of the Serogroup C Conjugate

The meningococcal serogroup C capsular saccharide is an α2→9-linked homopolymer of sialic acid (N-acetylneuraminic acid), typically with O-acetyl (OAc) groups at C-7 or C-8 residues:

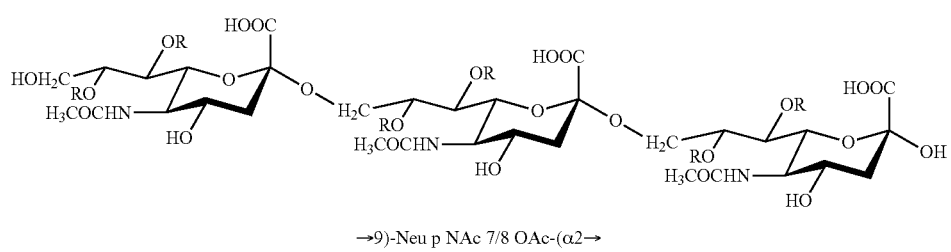

→9)-Neu p NAc 7/8 OAc-(α2→

R = —H or —COCH₃

Some MenC strains (~12% of invasive isolates) produce a polysaccharide that lacks this OAc group. The presence or absence of OAc groups generates unique epitopes, and the specificity of antibody binding to the saccharide may affect its bactericidal activity against O-acetylated (OAc−) and de-O-acetylated (OAc+) strains [7-9]. Licensed MenC conjugate vaccines include both OAc− (NeisVac-C™) and OAc+ (Menjugate™ & Meningitec™) saccharides.

According to the invention, either OAc+ or OAc− strains can be used.

Thus the invention provides a combination vaccine comprising (i) a diphtheria toxoid, (ii) a tetanus toxoid, (iii) cellular pertussis antigen, (iv) a hepatitis B virus surface antigen ('HBsAg'), (v) a *Haemophilus influenzae* type b capsular saccharide conjugated to a carrier protein, and (vi) *Neisseria meningitidis* serogroup C capsular saccharide conjugated to a carrier protein, characterised in that at least 50% of the sialic acid residues in the serogroup C capsular saccharide of (vi) are O-acetylated at the C-7 or C-8 position.

The invention also provides a combination vaccine comprising (i) a diphtheria toxoid, (ii) a tetanus toxoid, (iii) cellular pertussis antigen, (iv) a hepatitis B virus surface antigen ('HBsAg'), (v) a *Haemophilus influenzae* type b capsular saccharide conjugated to a carrier protein, and (vi) *Neisseria meningitidis* serogroup C capsular saccharide conjugated to a carrier protein, characterised in that the serogroup C capsular saccharide is from a OAc+ strain.

The invention also provides a combination vaccine comprising (i) a diphtheria toxoid, (ii) a tetanus toxoid, (iii) cellular pertussis antigen, (iv) a hepatitis B virus surface antigen ('HBsAg'), (v) a *Haemophilus influenzae* type b capsular saccharide conjugated to a carrier protein, and (vi) *Neisseria meningitidis* serogroup C capsular saccharide conjugated to a carrier protein, characterised in that the sialic acid residues in the serogroup C capsular saccharide of (vii) are not O-acetylated.

The invention also provides a combination vaccine comprising (i) a diphtheria toxoid, (ii) a tetanus toxoid, (iii) cellular pertussis antigen, (iv) a hepatitis B virus surface antigen ('HBsAg'), (v) a *Haemophilus influenzae* type b capsular saccharide conjugated to a carrier protein, and (vi) *Neisseria meningitidis* serogroup C capsular saccharide conjugated to a carrier protein, characterised in that the serogroup C capsular saccharide is from a OAc− strain.

These vaccines may also include (vii) *Neisseria meningitidis* serogroup A capsular saccharide conjugated to a carrier protein.

The invention also provides a process for preparing a combination vaccine that comprises (i) a diphtheria toxoid ('D'), (ii) a tetanus toxoid ('T'), (iii) cellular pertussis antigen ('Pw'), (iv) a hepatitis B virus surface antigen ('HBsAg'), (v) a *Haemophilus influenzae* type b capsular saccharide conjugated to a carrier protein, and (vi) *Neisseria meningitidis* serogroup C capsular saccharide conjugated to a carrier protein, characterised in that the process comprises the steps of: (a) combining a trivalent D-T-Pw component with a monovalent HBsAg component, to give a tetravalent D-T-Pw-HBsAg component; (b) combining the *H. influenzae* and *N. meningitidis* conjugates to give a mixed conjugate component, wherein at least 50% of the sialic acid residues in the serogroup C capsular saccharide of (vii) are O-acetylated at the C-7 or C-8 position.

The invention also provides a process for preparing a combination vaccine that comprises (i) a diphtheria toxoid ('D'), (ii) a tetanus toxoid ('T'), (iii) cellular pertussis antigen ('Pw'), (iv) a hepatitis B virus surface antigen ('HBsAg'), (v) a *Haemophilus influenzae* type b capsular saccharide conjugated to a carrier protein, and (vi) *Neisseria meningitidis* serogroup C capsular saccharide conjugated to a carrier protein, characterised in that the process comprises the steps of: (a) combining a trivalent D-T-Pw component with a monovalent HBsAg component, to give a tetravalent D-T-Pw-HBsAg component; (b) combining the *H. influenzae* and *N. meningitidis* conjugates to give a mixed conjugate component, wherein the sialic acid residues in the serogroup C capsular saccharide of (vii) are not O-acetylated.

The invention also provides a process for preparing a combination vaccine that comprises (i) a diphtheria toxoid ('D'), (ii) a tetanus toxoid ('T'), (iii) cellular pertussis antigen ('Pw'), (iv) a hepatitis B virus surface antigen ('HBsAg'), (v) a *Haemophilus influenzae* type b capsular saccharide conjugated to a carrier protein, and (vi) *Neisseria meningitidis* serogroup C capsular saccharide conjugated to a carrier protein, characterised in that the process comprises the steps of: (a) combining a trivalent D-T-Pw component with a monovalent HBsAg component, to give a tetravalent D-T-Pw-HBsAg component; (b) combining the *H. influenzae* and *N. meningitidis* conjugates to give a mixed conjugate component, wherein the serogroup C capsular saccharide is from a OAc− strain.

The invention also provides a process for preparing a combination vaccine that comprises (i) a diphtheria toxoid ('D'), (ii) a tetanus toxoid ('T'), (iii) cellular pertussis antigen ('Pw'), (iv) a hepatitis B virus surface antigen ('HBsAg'), (v) a *Haemophilus influenzae* type b capsular saccharide conjugated to a carrier protein, and (vi) *Neisseria meningitidis* serogroup C capsular saccharide conjugated to a carrier protein, characterised in that the process comprises the steps of: (a) combining a trivalent D-T-Pw component with a monovalent HBsAg component, to give a tetravalent D-T-Pw-HBsAg component; (b) combining the *H. influenzae* and *N. meningitidis* conjugates to give a mixed conjugate component, wherein the serogroup C capsular saccharide is from a OAc+ strain.

The vaccines made by these processes may also include (vii) *Neisseria meningitidis* serogroup A capsular saccharide conjugated to a carrier protein.

The invention also provides a conjugate mixture comprising (i) *Haemophilus influenzae* type b capsular saccharide conjugated to a carrier protein, (ii) *Neisseria meningitidis* serogroup A capsular saccharide conjugated to a carrier protein, and (iii) *Neisseria meningitidis* serogroup C capsular saccharide conjugated to a carrier protein, characterised in that the sialic acid residues in the MenC conjugate are not O-acetylated.

The invention also provides a conjugate mixture comprising (i) *Haemophilus influenzae* type b capsular saccharide conjugated to a carrier protein, (ii) *Neisseria meningitidis* serogroup A capsular saccharide conjugated to a carrier protein, and (iii) *Neisseria meningitidis* serogroup C capsular saccharide conjugated to a carrier protein, characterised in that the MenC capsular saccharide is from a OAc− strain.

The invention also provides a conjugate mixture comprising (i) *Haemophilus influenzae* type b capsular saccharide conjugated to a carrier protein, (ii) *Neisseria meningitidis* serogroup A capsular saccharide conjugated to a carrier protein, and (iii) *Neisseria meningitidis* serogroup C capsular saccharide conjugated to a carrier protein, characterised in that at least 50% of the sialic acid residues in the MenC conjugate are O-acetylated at the C-7 or C-8 position.

The invention also provides a conjugate mixture comprising (i) *Haemophilus influenzae* type b capsular saccharide conjugated to a carrier protein, (ii) *Neisseria meningitidis* serogroup A capsular saccharide conjugated to a carrier protein, and (iii) *Neisseria meningitidis* serogroup C capsular saccharide conjugated to a carrier protein, characterised in that the MenC capsular saccharide is from a OAc+ strain.

Where at least 50% of the sialic acid residues in the serogroup C conjugate are O-acetylated, the minimum percentage may be higher e.g. 60%, 70%, 80%, 90% or higher.

Preferred strains for production of serogroup C conjugates are OAc+ strains, preferably of serotype 16, preferably of serosubtype P1.7a,1. Thus C:16:P1.7a,1 OAc+ strains are preferred.

(5) O-Acetylation of the Serogroup A Conjugate

The meningococcal serogroup A capsular saccharide is a homopolymer of N-acetyl-mannosamine-phosphate linked $\alpha 1 \rightarrow 6$, with partial O-acetylation at the C-3 and C-4 positions:

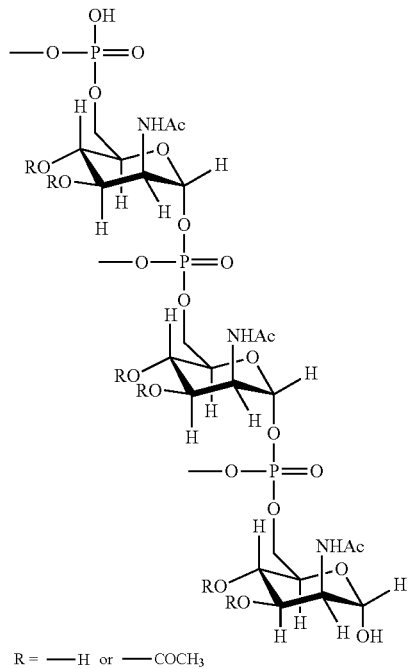

Acetylation at the C-3 position can be as high as 70-95%. Conditions used to purify the saccharide can result in de-O-acetylation (e.g. under basic conditions), but the invention seeks to retain OAc.

Thus the invention provides a combination vaccine comprising (i) a diphtheria toxoid, (ii) a tetanus toxoid, (iii) cellular pertussis antigen, (iv) a hepatitis B virus surface antigen ('HBsAg'), (v) a *Haemophilus influenzae* type b capsular saccharide conjugated to a carrier protein, and (vi) *Neisseria meningitidis* serogroup A capsular saccharide conjugated to a carrier protein, characterised in that at least 50% of the mannosamine residues in the serogroup A capsular saccharide are O-acetylated at the C-3 position. The vaccine may also include (vii) *Neisseria meningitidis* serogroup C capsular saccharide conjugated to a carrier protein, The invention also provides a process for preparing a combination vaccine that comprises (i) a diphtheria toxoid ('D'), (ii) a tetanus toxoid ('T'), (iii) cellular pertussis antigen ('Pw'), (iv) a hepatitis B virus surface antigen ('HBsAg'), (v) a *Haemophilus influenzae* type b capsular saccharide conjugated to a carrier protein, and (vi) *Neisseria meningitidis* serogroup A capsular saccharide conjugated to a carrier protein, characterised in that the process comprises the steps of: (a) combining a trivalent D-T-Pw component with a monovalent HBsAg component, to give a tetravalent D-T-Pw-HBsAg component; (b) combining the *H. influenzae* and *N. meningitidis* conjugates to give a mixed conjugate component, wherein at least 50% of the mannosamine residues in the serogroup A capsular saccharide are O-acetylated at the C-3 position.

The vaccine made by this processes may also include (vii) *Neisseria meningitidis* serogroup C capsular saccharide conjugated to a carrier protein.

The invention also provides a conjugate mixture comprising (i) *Haemophilus influenzae* type b capsular saccharide conjugated to a carrier protein, (ii) *Neisseria meningitidis* serogroup A capsular saccharide conjugated to a carrier protein, and (iii) *Neisseria meningitidis* serogroup C capsular saccharide conjugated to a carrier protein, characterised in that at least 50% of the mannosamine residues in the serogroup A capsular saccharide are O-acetylated at the C-3 position.

Where at least 50% of the mannosamine residues in the serogroup A conjugate are O-acetylated, the minimum percentage may be higher e.g. 60%, 70%, 80%, 90% or higher.

(6) Conjugate Dosing

Hib-conjugate antigens are not cheap to produce, and various strategies to economise their use have been developed [10-12]. One approach has been to give two doses conjugates at doses lower than the standard 10 μg/dose (typically fractions e.g. ½, ⅓, ¼, etc.) [10,12]. In ref. 12, for example, Hib-conjugates were administered at 5 μg/dose or 3.33 μg/dose i.e. ½ or ⅓ or the normal dose.

The same approach has been extended to Hib-conjugates within DTP-Hib vaccines. For example, reference 13 compares full-dose, half-dose and third-dose use of Hib-conjugate in combination with a DTwP vaccine and, although geometric mean concentrations of anti-PRP bodies were reduced in patients receiving combined DTP-Hib vaccines compared to separate administration of DTP and Hib, acceptable protective anti-Hib immune responses were seen in all cases. Reference 14 uses a 10-fold dilution of Hib-conjugate dosage by reconstituting a single Hib dose with a ten-dose vial of DTwP. Reference 2 discloses reconstitution of lyophilised Hib-conjugate at full dose, half-dose or quarter-dose using the TRITANPIX™ DTwP-HBsAg vaccine.

Similar dosing studies have not been reported for meningococcal conjugates in combination vaccines.

For the combination vaccines of the invention, an amount of between 8 μg and 12 μg (measured as saccharide) of the Hib and meningococcal conjugates has been selected. This amount can be present in a single unit dose, or can be present per milliliter of the vaccine.

Thus the invention provides a combination vaccine comprising (i) a diphtheria toxoid, (ii) a tetanus toxoid, (iii) cellular pertussis antigen, (iv) a hepatitis B virus surface antigen, (v) a *Haemophilus influenzae* type b capsular saccharide conjugated to a carrier protein, and (vi) at least one *Neisseria meningitidis* capsular saccharide conjugated to a carrier protein, characterised in that the vaccine contains between 8 μg/ml and 12 μg/ml of the *Haemophilus influenzae* type b capsular saccharide. It is preferred to include meningococcal conjugates for both of serogroups A and C.

The invention also provides a combination vaccine comprising (i) a diphtheria toxoid, (ii) a tetanus toxoid, (iii) cellular pertussis antigen, (iv) a hepatitis B virus surface antigen, (v) a *Haemophilus influenzae* type b capsular saccharide conjugated to a carrier protein, and (vi) *Neisseria meningitidis* serogroup A capsular saccharide conjugated to a carrier protein, characterised in that the vaccine contains between 8

μg/ml and 12 μg/ml of the meningococcal serogroup A capsular saccharide. The vaccine preferably also includes (vii) *Neisseria meningitidis* serogroup C capsular saccharide conjugated to a carrier protein.

The invention also provides a combination vaccine comprising (i) a diphtheria toxoid, (ii) a tetanus toxoid, (iii) cellular pertussis antigen, (iv) a hepatitis B virus surface antigen ('HBsAg'), (v) a *Haemophilus influenzae* type b capsular saccharide conjugated to a carrier protein, and (vi) *Neisseria meningitidis* serogroup C capsular saccharide conjugated to a carrier protein, characterised in that the vaccine contains between 8 μg/ml and 12 μg/ml of the meningococcal serogroup C capsular saccharide. The vaccine preferably also includes (vii) *Neisseria meningitidis* serogroup A capsular saccharide conjugated to a carrier protein.

The invention provides a combination vaccine comprising (i) a diphtheria toxoid, (ii) a tetanus toxoid, (iii) cellular pertussis antigen, (iv) a hepatitis B virus surface antigen, (v) a *Haemophilus influenzae* type b capsular saccharide conjugated to a carrier protein, and (vi) at least one *Neisseria meningitidis* capsular saccharide conjugated to a carrier protein, characterised in that the vaccine contains between 8 μg and 12 μg of the *Haemophilus influenzae* type b capsular saccharide per unit dose. It is preferred to include meningococcal conjugates for both of serogroups A and C.

The invention also provides a combination vaccine comprising (i) a diphtheria toxoid, (ii) a tetanus toxoid, (iii) cellular pertussis antigen, (iv) a hepatitis B virus surface antigen, (v) a *Haemophilus influenzae* type b capsular saccharide conjugated to a carrier protein, and (vi) *Neisseria meningitidis* serogroup A capsular saccharide conjugated to a carrier protein, characterised in that the vaccine contains between 8 μg and 12 μg of the meningococcal serogroup A capsular saccharide per unit dose. The vaccine preferably also includes (vii) *Neisseria meningitidis* serogroup C capsular saccharide conjugated to a carrier protein.

The invention also provides a combination vaccine comprising (i) a diphtheria toxoid, (ii) a tetanus toxoid, (iii) cellular pertussis antigen, (iv) a hepatitis B virus surface antigen ('HBsAg'), (v) a *Haemophilus influenzae* type b capsular saccharide conjugated to a carrier protein, and (vi) *Neisseria meningitidis* serogroup C capsular saccharide conjugated to a carrier protein, characterised in that the vaccine contains between 8 μg and 12 μg of the meningococcal serogroup C capsular saccharide per unit dose. The vaccine preferably also includes (vii) *Neisseria meningitidis* serogroup A capsular saccharide conjugated to a carrier protein.

Preferred vaccines have a saccharide dose of between 8 μg and 12 μg (per milliliter or per unit dose) for all three of the Hib, MenA and MenC conjugates.

(7) Extemporaneous Processes for Preparing Vaccines of the Invention

As mentioned above, vaccines of the invention can be prepared extemporaneously at the time of use by mixing together two components: (a) a first component comprising D, T, wP and HBsAg antigens; and (b) a second component comprising a Hib conjugate and at least one meningococcal conjugate. The two components are preferably packaged separately, and thus in general the invention provides a kit comprising: (a) a first component comprising D, T, wP and HBsAg antigens; and (b) a second component comprising a Hib conjugate and at least one meningococcal conjugate. This approach avoids the depolymerisation of conjugates that can occur during aqueous storage conditions, which is a particular problem for Hib and MenA conjugates, particularly when combined.

The two components (a) and (b) are packaged separately e.g. in separate vials. The contents of the first vial (containing D-T-wP-HBsAg) are preferably aqueous, and the contents of the second vial (containing the conjugates) are preferably lyophilised, such that vaccines of the invention can be prepared by reconstituting the lyophilised component with the aqueous component. Thus the invention provides a process for preparing a vaccine composition of the invention, comprising the steps of (a) providing a first component comprising D, T, wP and HBsAg antigens in aqueous form; (b) providing a second component comprising Hib and meningococcal conjugates in lyophilised form; and (c) mixing the first and second components to give the vaccine. The mixing step will typically take place at the time of use.

The invention also provides a process for preparing a kit of the invention, comprising the steps of: (a) obtaining or preparing a first component comprising D, T, wP and HBsAg antigens; (b) obtaining or preparing a second component comprising Hib and meningococcal conjugates; and (c) combining the two components in the form of a kit.

More specifically, the invention provides:

a kit comprising (a) a first component comprising D, T, wP and HBsAg antigens; and (b) a second component comprising a *H. influenzae* type b capsular saccharide conjugated to a carrier protein and at least one *N. meningitidis* capsular saccharide conjugated to a carrier protein, characterised in that the *H. influenzae* conjugate has a weight excess of carrier to saccharide with a weight ratio of carrier to saccharide of between 2:1 and 4:1.

a process for preparing a kit of the invention, comprising the steps of: (a) preparing a first component comprising D, T, wP and HBsAg antigens; (b) preparing a second component comprising a *H. influenzae* type b capsular saccharide conjugated to a carrier protein and at least one *N. meningitidis* capsular saccharide conjugated to a carrier protein, characterised in that the *H. influenzae* conjugate has a weight excess of carrier to saccharide with a weight ratio of carrier protein to saccharide of between 2:1 and 4:1; and (c) combining the two components in the form of a kit.

a kit comprising (i) a first component comprising D, T, wP and HBsAg antigens; and (ii) a second component comprising a *H. influenzae* type b capsular saccharide conjugated to a carrier protein and at least one *N. meningitidis* capsular saccharide conjugated to a carrier protein, characterised in that the *H. influenzae* conjugate is obtainable by a process comprising the steps of: (a) activating a *Haemophilus influenzae* type b capsular saccharide with cyanogen bromide, to give a cyanate ester; (b) adding an adipic hydrazide spacer to the cyanate ester, to give an activated saccharide; and (c) coupling the activated saccharide to a carrier protein by carbodiimide condensation.

a kit comprising (a) a first component comprising D, T, wP and HBsAg antigens; and (b) a second component comprising a *H. influenzae* type b capsular saccharide conjugated to a carrier protein and at least one *N. meningitidis* capsular saccharide conjugated to a carrier protein, characterised in that the *H. influenzae* conjugate includes a linker with one of the following two structures:

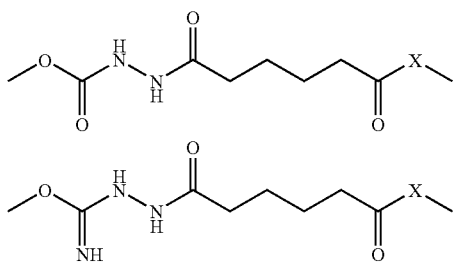

where —X— is selected from the group consisting of: —O—, —S— or —NH—.

a process for preparing a kit of the invention, comprising the steps of: (i) preparing a first component comprising D, T, wP and HBsAg antigens; (ii) preparing a second component comprising a *H. influenzae* type b capsular saccharide conjugated to a carrier protein and at least one *N. meningitidis* capsular saccharide conjugated to a carrier protein; and (iii) combining the two components in the form of a kit, characterised in that the *H. influenzae* conjugate is obtainable by a process comprising the steps of: (a) activating a *H. influenzae* type b capsular saccharide with cyanogen bromide, to give a cyanate ester; (b) adding an adipic hydrazide spacer to the cyanate ester, to give an activated saccharide; and (c) coupling the activated saccharide to a carrier protein by carbodiimide condensation.

a process for preparing a kit of the invention, comprising the steps of: (a) preparing a first component comprising D, T, wP and HBsAg antigens; (b) preparing a second component comprising a *H. influenzae* type b capsular saccharide conjugated to a carrier protein and at least one *N. meningitidis* capsular saccharide conjugated to a carrier protein; and (c) combining the two components in the form of a kit, characterised in that the *H. influenzae* conjugate includes a linker with one of the following two structures:

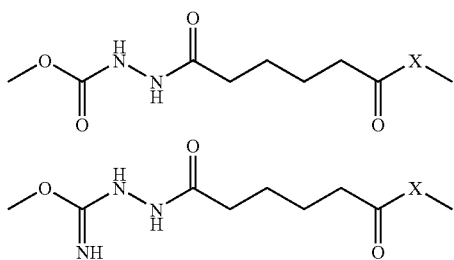

where —X— is selected from the group consisting of: —O—, —S— or —NH—.

a process for preparing a kit of the invention, comprising the steps of: (i) preparing a first component comprising D, T, wP and HBsAg antigens; (ii) preparing a second component comprising a *H. influenzae* type b capsular saccharide conjugated to a carrier protein and a *N. meningitidis* serogroup A capsular saccharide conjugated to a carrier protein, characterised in that the *N. meningitidis* serogroup A conjugate is obtainable by a process comprising the steps of: a) cyanylating a serogroup A capsular saccharide to give a cyanate ester; and (b) coupling the cyanate ester directly to a carrier protein.

a process for preparing a kit of the invention, comprising the steps of: (a) preparing a first component comprising D, T, wP and HBsAg antigens; (b) preparing a second component comprising a *H. influenzae* type b capsular saccharide conjugated to a carrier protein and a *N. meningitidis* serogroup C capsular saccharide conjugated to a carrier protein, characterised in that the *N. meningitidis* serogroup C conjugate is obtainable by a process comprising the steps of: a) cyanylating a serogroup C capsular saccharide to give a cyanate ester; and (b) coupling the cyanate ester directly to a carrier protein.

a process for preparing a kit of the invention, comprising the steps of: (i) preparing a first component comprising D, T, wP and HBsAg antigens; (ii) preparing a second component comprising a *H. influenzae* type b capsular saccharide conjugated to a carrier protein and a *N. meningitidis* serogroup A capsular saccharide conjugated to a carrier protein, characterised in that the *N. meningitidis* serogroup A conjugate is obtainable by a process comprising the steps of: (a) cyanylating a serogroup A capsular saccharide to give an cyanate ester; (b) reacting the cyanate ester with a bifunctional linker, to give an activated saccharide; and (c) coupling the activated saccharide to a carrier protein.

a process for preparing a kit of the invention, comprising the steps of: (i) preparing a first component comprising D, T, wP and HBsAg antigens; (ii) preparing a second component comprising a *H. influenzae* type b capsular saccharide conjugated to a carrier protein and a *N. meningitidis* serogroup C capsular saccharide conjugated to a carrier protein, characterised in that the *N. meningitidis* serogroup C conjugate is obtainable by a process comprising the steps of: (a) cyanylating a serogroup C capsular saccharide to give an cyanate ester; (b) reacting the cyanate ester with a bifunctional linker, to give an activated saccharide; and (c) coupling the activated saccharide to a protein carrier.

a kit comprising (a) a first component comprising D, T, wP and HBsAg antigens; and (b) a second component comprising a *H. influenzae* type b capsular saccharide conjugated to a carrier protein and a *N. meningitidis* serogroup C capsular saccharide conjugated to a carrier protein, characterised in that at least 50% of the sialic acid residues in the *N. meningitidis* serogroup C conjugate are O-acetylated at the C-7 or C-8 position.

a kit comprising (a) a first component comprising D, T, wP and HBsAg antigens; and (b) a second component comprising a *H. influenzae* type b capsular saccharide conjugated to a carrier protein and a *N. meningitidis* serogroup C capsular saccharide conjugated to a carrier protein, characterised in that the sialic acid residues in the *N. meningitidis* serogroup C conjugate are not O-acetylated.

a kit comprising (a) a first component comprising D, T, wP and HBsAg antigens; and (b) a second component comprising a *H. influenzae* type b capsular saccharide conjugated to a carrier protein and a *N. meningitidis* serogroup C capsular saccharide conjugated to a carrier protein, characterised in that the *N. meningitidis* serogroup C capsular saccharide is from a OAc+ strain.

a kit comprising (a) a first component comprising D, T, wP and HBsAg antigens; and (b) a second component comprising a *H. influenzae* type b capsular saccharide conjugated to a carrier protein and a *N. meningitidis* serogroup C capsular saccharide conjugated to a carrier protein, characterised in that the *N. meningitidis* serogroup C capsular saccharide is from a OAc− strain.

a kit comprising (a) a first component comprising D, T, wP and HBsAg antigens; and (b) a second component comprising a *H. influenzae* type b capsular saccharide conjugated to a carrier protein and a *N. meningitidis* serogroup A capsular saccharide conjugated to a carrier protein, characterised in that at least 50% of the mannosamine residues in the serogroup A capsular saccharide are O-acetylated at the C-3 position.

a process for preparing a kit of the invention, comprising the steps of: (a) combining a trivalent D-T-Pw component with a monovalent HBsAg component, to give a first kit component; and (b) combining a *H. influenzae* type b capsular saccharide conjugated to a carrier protein, a *N. meningitidis* serogroup A capsular saccharide conjugated to a carrier protein, and a *N. meningitidis* serogroup C capsular saccharide conjugated to a carrier protein, to give a second kit component.

The first component of a kit is preferably made by mixing a DTPw component with a HBsAg component. The second component of a kit is preferably a trivalent conjugate component comprising: (1) a *Haemophilus influenzae* capsular saccharide conjugated to a carrier protein; (2) a *Neisseria meningitidis* serogroup A capsular saccharide conjugated to a carrier protein; and (3) a *Neisseria meningitidis* serogroup C capsular saccharide conjugated to a carrier protein.

(8) Processes for Preparing Vaccines of the Invention

Preferred heptavalent vaccines of the invention comprise the seven antigenic components D, T, Pw, HBsAg, Hib-X, MenA-X and MenC-X. Although these can in principle be mixed in any order, it is particularly preferred, as described above, to prepare a first component (with the D, T, Pw and HBsAg antigens) and a second component (with the Hib, MenA and MenC conjugates), and to combine these two components at the time of use.

Moreover, it is preferred that the D-T-Pw-HBsAg component is prepared by mixing a D-T-Pw component with a HBsAg component. This order of mixing (i.e. adding HBsAg to an existing DTPw mixture, rather than adding HBsAg before any of the D, T or Pw antigens) has been found to be particularly useful for making combination vaccines, particularly where the individual components of the vaccine are adsorbed to aluminium salts. It is different from the order of mixing disclosed in reference 15, where a D-T-HBsAg mixture is initially made, with a Pw stock solution then being added. It is also different from the order of mixing in reference 16, where a Pw-HBsAg mixture is combined with a D-T mixture.

Thus the invention provides a process for preparing a combination vaccine that comprises (i) a diphtheria toxoid ('D'), (ii) a tetanus toxoid ('T'), (iii) a cellular pertussis antigen ('Pw'), (iv) a hepatitis B virus surface antigen ('HBsAg'), (v) a *Haemophilus influenzae* type b capsular saccharide conjugated to a carrier protein ('Hib-X'), (vi) a *Neisseria meningitidis* serogroup A capsular saccharide conjugated to a carrier protein ('MenA-X'), and (vii) a *Neisseria meningitidis* serogroup C capsular saccharide conjugated to a carrier protein ('MenC-X'), characterised in that the process comprises the steps of: (a) combining a trivalent D-T-Pw component with a monovalent HBsAg component, to give a tetravalent D-T-Pw-HBsAg component; (b) combining a Hib conjugate with at least one meningococcal conjugate, to give a mixed conjugate component; and (c) mixing the tetravalent D-T-Pw-HBsAg component with the mixed conjugate component, to give the combination vaccine.

The trivalent D-T-Pw component preferably includes an aluminium phosphate adjuvant and/or an aluminium hydroxide adjuvant. Most preferably, it includes both an aluminium phosphate adjuvant and an aluminium hydroxide adjuvant.

The monovalent HBsAg component is preferably adsorbed to an aluminium phosphate adjuvant [17]. The D and T toxoids are preferably adsorbed to an aluminium hydroxide adjuvant.

The mixed conjugate component preferably comprises conjugates from Hib & MenA, Hib & MenC or Hib & MenA & MenC.

Unlike the situation in vaccines such as INFANRIX HEXA™, it is preferred that none of the three conjugates in a conjugate component is adsorbed to an aluminium salt [2], and more preferably the conjugate component does not include an aluminium salt. Most preferred conjugate components are unadjuvanted. They may, however, contain sugars, such as lactose and/or sucrose.

The tetravalent D-T-Pw-HBsAg component is preferably in aqueous form, and the trivalent conjugate component is preferably in lyophilised form, for reconstitution by an aqueous D-T-Pw-HBsAg component in step (c). For making the tetravalent D-T-Pw-HBsAg component, the D-T-Pw and the HBsAg components are preferably both in aqueous form when mixed.

To prepare a trivalent conjugate component, three conjugates can be mixed in any order e.g. adding all three together, or mixing two (e.g. MenA+MenC, MenA+Hib, MenC+Hib) and then adding the third.

(9) Aluminium Adjuvants

As well as including antigens, vaccines of the invention typically include at least one aluminium salt adjuvant. The vaccines can include both aluminium hydroxide and aluminium phosphate adjuvants.

The invention provides a kit comprising: (a) a first component comprising D, T, wP and HBsAg antigens, and comprising both an aluminium hydroxide and an aluminium phosphate adjuvant; and (b) a second component comprising (i) a *H. influenzae* type b capsular saccharide conjugated to a carrier protein and (ii) at least one *N. meningitidis* capsular saccharide conjugated to a carrier protein.

Within the first component, HBsAg is preferably adsorbed to an aluminium phosphate adjuvant. The D and T toxoids are preferably adsorbed to an aluminium hydroxide adjuvant. The first component is preferably made by mixing a DTPw component with a HBsAg component. The DTPw component preferably includes both aluminium hydroxide and aluminium phosphate. The HBsAg component preferably contains aluminium phosphate.

Within the second component, preferably none of the conjugates is adsorbed to an aluminium salt, and more preferably the second component does not include an aluminium salt. Most preferred second components are unadjuvanted. They may, however, contain sugars, such as lactose or, preferably, sucrose.

The first component is preferably in aqueous form, and the second component is preferably in lyophilised form. Thus the first component can be used to reconstitute the second component to give a vaccine of the invention.

(10) Carrier-Saccharide Linkage in the Meningococcal Conjugates using a Spacer

The Hib conjugate described above is linked to the carrier protein by a spacer. Spacers can also be used in the meningococcal conjugates, but direct linkage is preferred (see above). Where spacers are used in combination with cyanylation, the general scheme is to prepare a cyanate ester as described above. The ester is then activated by reaction with one functional group of a bifunctional linker (preferably a homo-bifunctional linker), to leave the other functional groups remaining for linkage to the carrier.

Thus the invention provides a combination vaccine comprising (i) a diphtheria toxoid, (ii) a tetanus toxoid, (iii) cellular pertussis antigen, (iv) a hepatitis B virus surface antigen ('HBsAg'), (v) a *Haemophilus influenzae* type b capsular saccharide conjugated to a carrier protein, and (vi) *Neisseria meningitidis* serogroup A capsular saccharide conjugated to a carrier protein, characterised in that the serogroup A conjugate of (vi) is obtainable by a process comprising the steps of: (a) cyanylating a serogroup A capsular saccharide to give an cyanate ester; (b) reacting the cyanate ester with a bifunctional linker, to give an activated saccharide; and (c) coupling the activated saccharide to a carrier protein. The vaccine may also include (vii) *Neisseria meningitidis* serogroup C capsular saccharide conjugated to a carrier protein, The invention also provides a process for preparing a conjugate mixture comprising (i) *Haemophilus influenzae* type b capsular saccharide conjugated to a carrier protein, (ii) *Neisseria meningitidis* serogroup A capsular saccharide conjugated to a carrier protein, and (iii) *Neisseria meningitidis* serogroup C capsular saccharide conjugated to a carrier protein, characterised in that the serogroup A conjugate is produced by a process comprising the steps of: (a) cyanylating a serogroup A capsular saccharide to give a cyanate ester; (b) reacting the cyanate ester with a bifunctional linker, to give an activated saccharide; and (c) coupling the activated saccharide to a carrier protein.

The invention provides a combination vaccine comprising (i) a diphtheria toxoid, (ii) a tetanus toxoid, (iii) cellular pertussis antigen, (iv) a hepatitis B virus surface antigen ('HBsAg'), (v) a *Haemophilus influenzae* type b capsular saccharide conjugated to a carrier protein, and (vi) *Neisseria meningitidis* serogroup C capsular saccharide conjugated to a carrier protein, characterised in that the serogroup C conjugate of (vii) is obtainable by a process comprising the steps of: (a) cyanylating a serogroup C capsular saccharide to give an cyanate ester; (b) reacting the cyanate ester with a bifunctional linker, to give an activated saccharide; and (c) coupling the activated saccharide to a carrier protein. The vaccine may also include (vii) *Neisseria meningitidis* serogroup A capsular saccharide conjugated to a carrier protein.

The invention also provides a process for preparing a conjugate mixture comprising (i) *Haemophilus influenzae* type b capsular saccharide conjugated to a carrier protein, (ii) *Neisseria meningitidis* serogroup A capsular saccharide conjugated to a carrier protein, and (iii) *Neisseria meningitidis* serogroup C capsular saccharide conjugated to a carrier protein, characterised in that the serogroup C conjugate of (iii) is produced by a process comprising the steps of: (a) cyanylating a serogroup C capsular saccharide to give a cyanate ester; (b) reacting the cyanate ester with a bifunctional linker, to give an activated saccharide; and (c) coupling the activated saccharide to a carrier protein.

The invention also provides vaccines and processes in which both serogroup A and serogroup C conjugates are prepared in this manner and are then combined.

Any suitable bifunctional linker can be used, provided that it has one functional group for covalent attachment to the cyanylated meningococcal saccharide and one functional group for attaching to the carrier. The two functional groups may be the same (i.e. a homobifunctional linker) or they may be different (i.e. a heterobifunctional linker), depending on the groups to which attachment is desired.

(11) Process for Addition of a Preservative

Vaccines typically contain preservatives in order to prevent dangerous microbial growth. In a combination vaccine formed by mixing various components then the skilled person must choose where and when to include the preservative. According to the invention, different components contain different preservatives.

Thus the invention provides a process for preparing a combination vaccine that comprises (i) a diphtheria toxoid ('D'), (ii) a tetanus toxoid ('T'), (iii) a cellular pertussis antigen ('Pw'), (iv) a hepatitis B virus surface antigen ('HBsAg'), (v) a *Haemophilus influenzae* type b capsular saccharide conjugated to a carrier protein, (vi) at least one *Neisseria meningitidis* capsular saccharide conjugated to a carrier protein, and (vii) a mercurial preservative, characterised in that the process comprises the steps of: (a) combining a trivalent D-T-Pw component with a monovalent HBsAg component, to give a tetravalent D-T-Pw-HBsAg component, wherein the D-T-Pw component also contains the preservative; (b) combining *H. influenzae* and *N. meningitidis* conjugates to give a mixed conjugate component; and (c) mixing the D-T-Pw-HBsAg component with the mixed conjugate component, to give the combination vaccine.

The invention provides a process for preparing a kit of the invention, comprising the steps of: (a) combining a trivalent D-T-Pw component with a monovalent HBsAg component, wherein the D-T-Pw component includes a mercurial preservative, to give a first kit component; and (b) combining a *Haemophilus influenzae* type b capsular saccharide conjugated to a carrier protein with at least one *Neisseria meningitidis* capsular saccharide conjugated to a carrier protein, to give a second kit component.

As an alternative step (a) in these processes, the first kit component can be prepared by mixing (i) a trivalent D-T-Pw component (ii) a HBsAg and (iii) a separate preservative, wherein the preservative of (iii) is not present (ii).

The mercurial preservative may be thiomersal (also known as thimerosal or merthiolate) or timerfonate. The mixed conjugate component (and the second kit component) may or may not include the preservative. It preferably does not include the preservative. The monovalent HBsAg component may or may not include the preservative. If a mercurial preservative has been used then a purified HBsAg may be subjected to dialysis (e.g. with cysteine) before being used to make the combination vaccine [18].

The mixed conjugate component preferably includes a Hib conjugate, a MenA conjugate and a MenC conjugate.

The invention also provides a process for preparing a combination vaccine that comprises (i) a diphtheria toxoid ('D'), (ii) a tetanus toxoid ('T'), (iii) a cellular pertussis antigen ('Pw'), (iv) a hepatitis B virus surface antigen ('HBsAg'), (v) a *Haemophilus influenzae* type b capsular saccharide conjugated to a carrier protein, (vi) at least one *Neisseria meningitidis* capsular saccharide conjugated to a carrier protein, and (vii) a 2-phenoxyethanol preservative, characterised in that the process comprises the steps of: (a) combining a trivalent D-T-Pw component with a monovalent HBsAg component, to give a tetravalent D-T-Pw-HBsAg component, wherein the D-T-Pw component does not contain 2-phenoxyethanol; (b) combining *H. influenzae* and *N. meningitidis* conjugates to give a mixed conjugate component; and (c) mixing the D-T-Pw-HBsAg component with the mixed conjugate component, to give the combination vaccine.

The invention provides a process for preparing a kit of the invention, comprising the steps of: (a) combining a trivalent D-T-Pw component with a monovalent HBsAg component, wherein the D-T-Pw component does not include a 2-phenoxyethanol preservative, to give a first kit component; and (b) combining a *Haemophilus influenzae* type b capsular saccharide conjugated to a carrier protein with at least one *Neis-* seria meningitidis capsular saccharide conjugated to a carrier protein, to give a second kit component.

As an alternative step (a) in these processes, the first kit component can be prepared by mixing (i) a trivalent D-T-Pw component (ii) a HBsAg and (iii) a separate 2-phenoxyethanol preservative, wherein the preservative of (iii) is not present (i).

The mixed conjugate component (and the second kit component) may or may not include 2-phenoxyethanol preservative. It preferably does not include the preservative. The monovalent HBsAg component may or may not include 2-phenoxyethanol preservative.

(12) Removal of Impurities from Conjugates

Conjugation chemistry is not always precise or stoichiometric, and can produce side products that are not desirable in a final vaccine product. The invention provides methods for assaying and/or removing these side products when preparing a mixed conjugate component. This component can be used to make vaccines of the invention, or as a component of kits of the invention.

The invention provides a process for preparing a conjugate mixture that comprises (i) a *Haemophilus influenzae* type b capsular saccharide conjugated to a carrier protein, (ii) *Neisseria meningitidis* serogroup A capsular saccharide conjugated to a carrier protein, and (iii) *Neisseria meningitidis* serogroup C capsular saccharide conjugated to a carrier protein, characterised in that the process comprises the steps of: (a) conjugating a Hib capsular saccharide to tetanus toxoid using EDAC, and then removing EDU; (b) conjugating a MenA capsular saccharide to a protein carrier using a CDAP reagent, and then removing DMAP; (c) conjugating a MenC capsular saccharide to a protein carrier using a CDAP reagent, and then removing DMAP; and (d) mixing the Hib conjugate from step (a), the MenA conjugate from step (b) and the MenC conjugate from step (c) to give the conjugate mixture.

After the mixing step, the conjugate mixture can be lyophilised e.g. to give a component for use in kits of the invention. Prior to lyophilisation, the pH of the trivalent component can be reduced e.g. to within the range 6.0±0.5, or about 6.1.

'EDAC' is 1-ethyl-3-(3-dimethylaminopropyl)carbodiimide, a water-soluble carbodiimide that has been used to crosslink biological substances that contain carboxylate acids and primary amines (see above). It will typically be used as the hydrochloride salt.

'EDU' is N-ethyl-N'-(3-dimethylaminopropyl)urea, a soluble reaction product of EDAC coupling:

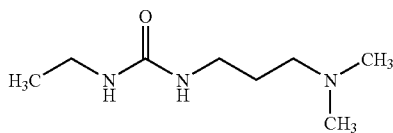

EDU and excess EDAC can both be removed after a conjugation reaction by washing with dilute acid or water. [19].

'CDAP' reagents include the 1-cyano-4-(dimethylamino)-pyridinium group and are used cyanylating reagents. They are preferably used as the tetrafluoroborate salt:

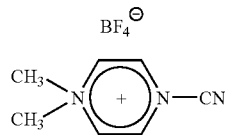

'DMAP' is 4-dimethylamino-pyridin, a reaction product of CDAP cyanylation:

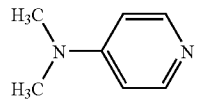

DMAP can be removed by gel filtration, gel permeation chromatography, etc. A gel permeation chromatography column can be used to separate conjugates, unreacted carrier, unreacted saccharide unreacted CDAP, unreacted glycine and DMAP in a single run, to give purified conjugate.

The conjugation reactions may involve the use of linkers, etc., as described above (e.g. the use of an adipic hydrazide spacer for preparation of Hib-T).

The invention also provides a process for preparing a conjugate mixture that comprises (i) a *Haemophilus influenzae* type b capsular saccharide conjugated to a carrier protein, (ii) *Neisseria meningitidis* serogroup A capsular saccharide conjugated to a carrier protein, and (iii) *Neisseria meningitidis* serogroup C capsular saccharide conjugated to a carrier protein, characterised in that the process comprises the steps of: (a) conjugating a Hib capsular saccharide to a carrier protein using EDAC; (b) conjugating a MenA capsular saccharide to a protein carrier using a CDAP reagent; (c) conjugating a MenC capsular saccharide to a protein carrier using a CDAP reagent; (d) mixing the Hib conjugate from step (a), the MenA conjugate from step (b) and the MenC conjugate from step (c) to give the conjugate mixture; and (e) removing EDU and/or DMAP from the conjugate mixture.

The invention also provides a process for preparing a conjugate mixture that comprises (i) a *Haemophilus influenzae* type b capsular saccharide conjugated to a carrier protein, (ii) *Neisseria meningitidis* serogroup A capsular saccharide conjugated to a carrier protein, and (iii) *Neisseria meningitidis* serogroup C capsular saccharide conjugated to a carrier protein, characterised in that the process comprises the steps of: (a) coupling a Hib capsular saccharide to tetanus toxoid using EDAC, and then assaying EDU; (b) coupling a MenA capsular saccharide to a protein carrier using a CDAP reagent, and then assaying DMAP; and (c) coupling a MenC capsular saccharide to a protein carrier using a CDAP reagent, and then assaying DMAP. The process will typically include the further step of: (d) mixing the Hib conjugate from step (a), the MenA conjugate from step (b) and the MenC conjugate from step (c) to give the conjugate mixture.

The invention also provides a process for preparing a conjugate mixture that comprises (i) a *Haemophilus influenzae* type b capsular saccharide conjugated to a carrier protein, (ii) *Neisseria meningitidis* serogroup A capsular saccharide conjugated to a carrier protein, and (iii) *Neisseria meningitidis* serogroup C capsular saccharide conjugated to a carrier protein, characterised in that the process comprises the steps of: (a) coupling a Hib capsular saccharide to tetanus toxoid using EDAC; (b) coupling a MenA capsular saccharide to a protein carrier using a CDAP reagent; and (c) coupling a MenC capsular saccharide to a protein carrier using a CDAP reagent; (d) mixing the Hib conjugate from step (a), the MenA conjugate from step (b) and the MenC conjugate from step (c) to give the conjugate mixture; and (e) assaying EDU and/or DMAP in the conjugate mixture.

The invention also provides a process for preparing a conjugate mixture that comprises (i) a *Haemophilus influenzae* type b capsular saccharide conjugated to a carrier protein, (ii) *Neisseria meningitidis* serogroup A capsular saccharide conjugated to a carrier protein, and (iii) *Neisseria meningitidis* serogroup C capsular saccharide conjugated to a carrier protein, characterised in that the process comprises the steps of: (a) conjugating a Hib capsular saccharide to a carrier protein using EDAC; (b) conjugating a MenA capsular saccharide to a protein carrier using EDAC; (c) conjugating a MenC capsular saccharide to a protein carrier using EDAC; (d) mixing the Hib conjugate from step (a), the MenA conjugate from step (b) and the MenC conjugate from step (c) to give the conjugate mixture; and (e) removing EDU from the conjugate mixture.

The EDAC/EDU protocol is particularly suitable where tetanus toxoid is the carrier protein. The CDAP/DMAP protocol is particularly suitable where protein D is the carrier protein.

(13) Combinations of Characterising Features

Sections (1) to (12) above include various characterising features of the invention:

| Characterising feature |
|---|
| (1) Weight ratio of saccharide to carrier in the Hib conjugate is between 1:2.5 and 1:3.5 |
| (2) Activation of Hib with CNBr, then coupling with an adipic acid linker |
| (3) Cyanylation of a meningococcal capsular saccharide to give a cyanate ester, then coupling the cyanate ester to a protein carrier directly. |
| (4) O-acetylation status of serogroup C meningococcus |
| (5) O-acetylation status of serogroup A meningococcus |
| (6) Conjugate doses between 8 μg and 12 μg |
| (7) Extemporaneous preparation of the vaccines, and kits |
| (8) Preparation by mixing D-T-Pw with HBsAg, and then mixing the D-T-Pw-HBsAg with MenA-MenC-Hib |
| (9) D, T, wP & HBsAg are kit component with Al hydroxide and phosphate adjuvants |
| (10) Coupling of meningococcal capsular saccharide to carrier using a bifunctional linker |
| (11) Inclusion of a preservative in the HBsAg component |
| (12) Removal and/or assaying of EDU and/or DMAP after using EDAC and/or DMAP |

Although these twelve characterising features are independent from each other, they can also be combined with each other. Thus the invention provides all possible 2-way, 3-way, 4-way, 5-way, 6-way, 7-way, 8-way, 9-way, 10-way, and 11-way combinations of features (1) to (12), as well as the combination of all 12 features.

Particularly preferred combinations include:
 a. (1)&(2)
 b. (1) & (2) & (6)
 c. (1) & (2) & (12)
 d. (1)&(2)&(6)&(12)
 e. (3) & (4)
 f. (3) & (5)
 g. (3) & (4) & (5)
 h. (3) & (4) & (6)
 i. (3) & (5) & (6)
 j. (3)&(4)&(5)&(6)
 k. (8) & (9)
 l. (8) & (11)
 m. Any of a. to l. in combination with (12)
 n. Any of a. to m. in combination with (7)
 o. Any of a. to n. in combination with (8)
 p. Any of a. to o. in combination with (9)
 q. Any of a. to p. in combination with (11)

Combinations e. and f. (and then g., h., i. & j.) is advantageous because, where CDAP is used, delicate acetyl groups on the meningococcal saccharides can be retained. Combination k. is advantageous because the correct order of mixing adjuvants and antigens can be critical to adsorption, and thus to efficacy and to long term storage stability. Combination l. is advantageous because it minimises the need to add preservative at multiple stages during production.

(14) The Diphtheria Toxoid

Diphtheria is caused by *Corynebacterium diphtheriae*, a Gram-positive non-sporing aerobic bacterium. This organism expresses a prophage-encoded ADP-ribosylating exotoxin ('diphtheria toxin'), which can be treated (e.g. using formalin or formaldehyde) to give a toxoid that is no longer toxic but that remains antigenic and is able to stimulate the production of specific anti-toxin antibodies after injection. Diphtheria toxoids are disclosed in more detail in chapter 13 of reference 1. Preferred diphtheria toxoids are those prepared by formaldehyde treatment. The diphtheria toxoid can be obtained by growing *C. diphtheriae* in growth medium (e.g. Fenton medium, or Linggoud & Fenton medium), which may be supplemented with bovine extract, followed by formaldehyde treatment, ultrafiltration and precipitation. The toxoided material may then be treated by a process comprising sterile filtration and/or dialysis.

The diphtheria toxoid is preferably adsorbed onto an aluminium hydroxide adjuvant.

Preferably, the diphtheria toxoid component is substantially free from any mercurial preservatives.

Quantities of diphtheria toxoid can be expressed in international units (IU). For example, the NIBSC supplies the 'Diphtheria Toxoid Adsorbed Third International Standard 1999' [20,21], which contains 160 IU per ampoule. As an alternative to the IU system, the 'Lf' unit ("flocculating units" or the "limes flocculating dose") is defined as the amount of toxoid which, when mixed with one International Unit of antitoxin, produces an optimally flocculating mixture [22]. For example, the NIBSC supplies 'Diphtheria Toxoid, Plain' [23], which contains 300 LF per ampoule, and also supplies 'The 1st International Reference Reagent For Diphtheria Toxoid For Flocculation Test' [24] which contains 900 LF per ampoule.

Where bovine materials are used in the culture of *C. diphtheriae*, they should be obtained from sources that are free from bovine spongiform encephalopathy (BSE) or from other transmissible spongiform encephalopathies (TSEs).

The ratio of diphtheria toxoid to tetanus toxoid in vaccines of the invention is usually between 2:1 and 3:1 (measured in Lf units), preferably between 2.4:1 and 2.6:1, and is more preferably 2.5:1.

The amount of diphtheria toxoid in vaccines of the invention is typically at least 30 IU/dose.

(15) The Tetanus Toxoid

Tetanus is caused by *Clostridium tetani*, a Gram-positive, spore-forming *bacillus*. This organism expresses an endopeptidase ('tetanus toxin'), which can be treated to give a toxoid that is no longer toxic but that remains antigenic and is able to stimulate the production of specific anti-toxin antibodies after injection. Tetanus toxoids are disclosed in more detail in chapter 27 of reference 1. Preferred tetanus toxoids are those prepared by formaldehyde treatment. The tetanus toxoid can be obtained by growing *C. tetani* in growth medium (e.g. a Latham medium derived from bovine casein), followed by formaldehyde treatment, ultrafiltration and precipitation. The material may then be treated by a process comprising sterile filtration and/or dialysis.

The tetanus toxoid may be adsorbed onto an aluminium hydroxide adjuvant, but this is not necessary (e.g. adsorption of between 0-10% of the total tetanus toxoid can be used).

Preferably, the tetanus toxoid component is substantially free from any mercurial preservatives.

Quantities of tetanus toxoid can be expressed in international units (IU). For example, the NIBSC supplies the 'Tetanus Toxoid Adsorbed Third International Standard 2000' [25, 26], which contains 469 IU per ampoule. As an alternative to the IU system, the 'Lf' unit ("flocculating units" or the "limes flocculating dose") is defined as the amount of toxoid which, when mixed with one International Unit of antitoxin, produces an optimally flocculating mixture [22]. For example, the NIBSC supplies 'The 1st International Reference Reagent for Tetanus Toxoid For Flocculation Test' [27] which contains 1000 LF per ampoule.

Where bovine materials are used in the culture of *C. tetani*, they should be obtained from sources that are free from bovine spongiform encephalopathy (BSE) or from other transmissible spongiform encaphalopathies (TSEs).

The ratio of tetanus toxoid to diphtheria toxoid in vaccines of the invention is usually between 1:2 and 1:3 (measured in Lf units), preferably between 1:2.4 and 1:2.6, and is more preferably 1:2.5.

The amount of tetanus toxoid in vaccines of the invention is typically at least 60 IU/dose.

(16) The Cellular Pertussis Antigen

Pertussis antigens in vaccines are either cellular (whole cell) or acellular. The invention uses cellular pertussis antigens, in the form of inactivated *B. pertussis* cells. Preparation of cellular pertussis antigens is well documented [e.g. see chapter 21 of reference 1] e.g. it may be obtained by heat inactivation of phase I culture of *B. pertussis*.

The cellular pertussis antigen may be adsorbed onto or mixed with an aluminium phosphate adjuvant.

Quantities of wP antigens can be expressed in international units (IU). For example, the NIBSC supplies the 'Third International Standard For Pertussis Vaccine' [28], which contains 46 IU per ampoule. Each ampoule contains the freeze-dried residue of 2.0 ml aliquots of an aqueous solution which contained 10 liters of bacterial suspension (equivalent to 180 opacity units in terms of the U.S. Opacity Standard) diluted with eight liters of M/15 Sorensen's buffer pH 7.0. As an alternative to the IU system, the 'OU' unit ("opacity units") is also used (e.g. 4 OU may be about 1 IU).

The amount of wP antigen in vaccines of the invention is typically at least 4 IU/dose.

(17) The Hepatitis B Surface Antigen

Hepatitis B virus (HBV) is one of the known agents which causes viral hepatitis. The HBV virion consists of an inner core surrounded by an outer protein coat or capsid. The viral core contains the viral DNA genome. The major component of the capsid is a protein known as HBV surface antigen or, more commonly, 'HBsAg', a 226-amino acids with a molecular weight of ~24 kDa. All existing hepatitis B vaccines contain HBsAg, and when this antigen is administered to a vaccinee it stimulates the production of anti-HBsAg antibodies which protect against HBV infection.

For vaccine manufacture, HBsAg can be made in two ways. The first method involves purifying the antigen in particulate form from the plasma of chronic hepatitis B carriers, as large quantities of HBsAg are synthesized in the liver and released into the blood stream during an HBV infection. The second way involves expressing the protein by recombinant DNA methods. HBsAg for use with the method of the invention may be prepared in either way, but it is preferred to use HBsAg which has been recombinantly expressed. In particular, it is preferred that the HBsAg is prepared by expression in a yeast, such as a *Saccharomyces* (such as *S. cerevisiae*) or a *Hanensula* (such as *H. polymorpha*).

Yeast-expressed HBsAg will generally be non-glycosylated.

The HBsAg will generally be in the form of substantially-spherical particles (average diameter of about 20 nm), including a lipid matrix comprising phospholipids. Yeast-expressed HBsAg particles may include phosphatidylinositol, which is not found in natural HBV virions. The particles may also include a non-toxic amount of LPS in order to stimulate the immune system [29].

The HBsAg is preferably from IBV subtype adw2.

Although HBsAg may be adsorbed to an aluminium hydroxide adjuvant in the final vaccine (as in the well-known ENGERIX-B™ product), or may remain unadsorbed, it will generally be adsorbed to an aluminium phosphate adjuvant prior to being used in the process of the invention [17].

Quantities of HBsAg are typically expressed in micrograms.

A typical amount of HBsAg per vaccine dose is 10 μg.

(18) The Hib Conjugate

The *H. influenzae* type B antigen used in vaccines of the invention comprises a Hib capsular saccharide antigen. Saccharide antigens from *H. influenzae* b are well known [e.g. chapter 14 of ref. 1]. The Hib saccharide is conjugated to a carrier protein in order to enhance its immunogenicity, especially in children. The preparation of Hib capsular saccharide is well documented [e.g. references 30 to 39].

As shown in Table 14-7 of reference 1, various different linkage carrier proteins have been used in Hib conjugates. The PRP-D product uses a diphtheria toxoid carrier protein, and this carrier can also be used according to the invention. The HbOC product uses a CRM197 carrier protein, and this carrier can also be used according to the invention. The PRP-OMP product uses an outer membrane protein complex from serogroup B meningococcus as the carrier, and this carrier can also be used according to the invention. The PRP-T product uses a tetanus toxoid carrier protein, and this carrier can also be used according to the invention. *H. influenzae* protein D (see below) can also be used as the carrier for the Hib conjugate.

Preferred Hib conjugates used according to the present invention use tetanus toxoid as the carrier protein, to give the product commonly referred to as 'PRP-T'. This is the conjugate present in the HIBERIX™ product.

The carrier protein in the Hib conjugate is preferably different from the carrier protein(s) in the meningococcal conjugate(s), but the same carrier can be used in some embodiments.

The saccharide moiety of the conjugate may comprise full-length polyribosylribitol phosphate (PRP) as prepared from Hib bacteria, and/or it may comprise fragments of full-length PRP.

Conjugates with a saccharide:protein ratio (w/w) of between 1:5 (i.e. excess protein) and 5:1 (i.e. excess saccharide) may be used e.g. ratios between 1:2 and 5:1 and ratios between 1:1.25 and 1:2.5. In preferred vaccines, however, the weight ratio of saccharide to carrier protein is between 1:2.5 and 1:3.5.

In vaccines where tetanus toxoid is present both as an antigen and as a carrier protein then the weight ratio of saccharide to carrier protein in the conjugate may be between 1:0.3 and 1:2 [5].

Ignoring tetanus toxoid included as an antigen, unconjugated carrier is preferably no more than 5% of the total amount of the carrier protein in the composition as a whole, and more preferably present at less than 2% by weight.

Administration of the Hib antigen preferably results in an anti-PRP antibody concentration of ≥0.15 μg/ml, and more preferably ≥1 μg/ml. These are the standard acceptable response thresholds.

Amounts of Hib conjugates are generally given in terms of mass of saccharide (i.e. the dose of the conjugate (carrier+ saccharide) as a whole is higher than the stated dose) in order to avoid variation due to choice of carrier. A typical amount of Hib saccharide per vaccine dose is 10 μg.

Hib conjugates may be lyophilised prior to their use according to the invention. Further components may also be added prior to freeze-drying e.g. as stabilizers. Preferred stabilizers for inclusion are lactose, sucrose and mannitol, as well as mixtures thereof e.g. lactose/sucrose mixtures, sucrose/mannitol mixtures, etc. The final vaccine may thus contain lactose and/or sucrose. Using a sucrose/mannitol mixture can speed up the drying process.

(19) The Meningococcal Conjugates

The meningococcal antigens used in vaccines of the invention comprise capsular saccharide antigens conjugated to carrier proteins. Saccharide antigens from *N. meningitidis* are well known: a bivalent vaccine MENCEVAX AC™ and a tetravalent vaccine MENCEVAX ACWY™ have been known for many years [40, 41]. Moreover, conjugate vaccines against serogroup C have been approved for human use, and include MENJUGATE™ [42], MENINGITEC™ and NEISVAC-C™. Mixtures of conjugates from serogroups A+C are known [43, 44] and mixtures of conjugates from serogroups A+C+W135+Y have been reported [45-48].

The meningococcal saccharide(s) used in the products and processes of the invention can be from one or more of serogroups A, C, W135 and Y e.g. A+C, A+W135, A+Y, C+W135, C+Y, W135+Y, A+C+W135, A+C+Y, C+W135+Y, A+C+W135+Y. It is preferred to use at least the serogroup C saccharide, and preferably to use the saccharides from both of serogroups A and C.

The invention may use any suitable meningococcal conjugates, with any suitable linkage chemistry and any suitable spacers (except where specific details are given).

The MENJUGATE™ and MENINGITEC™ products use a CRM197 carrier protein, and this carrier can also be used according to the invention. The NEISVAC-C™ product uses a tetanus toxoid carrier protein, and this carrier can also be used according to the invention. A particularly preferred carrier protein for the meningococcal conjugates is protein D from *Haemophilus influenzae*, which is not present in any existing approved conjugate vaccines. This protein is described in detail in references 49 & 50, and its use as a carrier protein in conjugates is described in reference 51. The term "protein D" includes fragments of the native full-length protein, as disclosed in reference 51, and also fusion proteins comprising either full-length protein D or these fragments (e.g. a fusion of a fragment of influenza virus NS1 protein and a fragment of protein D). The fragments will retain the ability to convert a T-independent saccharide antigens into a T-dependent antigen when conjugated thereto. Typical fragments will include at least the N-terminal ⅓ of protein D. The protein can conveniently be expressed in *E. coli* [50], and this recombinant material is preferred for use with the invention [51].

Where a protein D carrier is used, the conjugates are referred to as 'MenA-D' and 'MenC-D'.

It is preferred that separate meningococcal conjugates should use separate carrier proteins (cf. reference 52), but it is preferred that these separate carriers should be the same as each other e.g. all meningococcal conjugates in the composition should use a tetanus toxoid carrier, or all meningococcal conjugates in the composition should use a protein D carrier, etc.

The carrier protein(s) in the meningococcal conjugate(s) is/are preferably different from the carrier protein in the Hib conjugate, but the same carrier can be used in some embodiments.

The saccharide moiety of the conjugate may comprise full-length saccharides as prepared from meningococci, and/or it may comprise fragments of full-length saccharides.

Meningococcal conjugates with a saccharide:protein ratio (w/w) of between 1:10 (i.e. excess protein) and 10:1 (i.e. excess saccharide) may be used e.g. ratios between 1:5 and 5:1, between 1:2.5 and 2.5:1, or between 1:1.25 and 1.25:1.

Administration of the meningococcal conjugates preferably results in an increase in serum bactericidal assay (SBA) titre for the relevant serogroup of at least 4-fold, and preferably at least 8-fold. SBA titres can be measured using baby rabbit complement or human complement [53].

Concentrations of meningococcal conjugates are generally given in terms of mass of saccharide (i.e. the dose of the conjugate (carrier+saccharide) as a whole is higher than the stated dose) in order to avoid variation due to choice of carrier. A typical amount of each meningococcal saccharide per vaccine dose is about 5 μg or about 10 μg.

Meningococcal conjugates may be lyophilised prior to their use according to the invention. Further components may also be added prior to freeze-drying e.g. as stabilizers. Preferred stabilizers for inclusion are lactose and/or sucrose. The final vaccine may thus contain lactose and/or sucrose.

(20) Conjugate Mixtures

The invention provides conjugate mixtures and processes for their preparation. These typically comprise a mixture of (i) a Hib conjugate, (ii) a MenA conjugate and (iii) a MenC conjugate. The conjugate mixtures can be used as vaccines themselves and also as components for mixing with other antigens to make combination vaccines.

The conjugate mixture can contain more than three conjugates, but it is preferably a trivalent conjugate mixture. Pentavalent conjugate mixtures, further comprising conjugated capsular saccharides from meningococcal serogroups W135 and Y can also be prepared.

The conjugate mixture is preferably in lyophilised form.

The conjugate mixture preferably comprises none of the following antigens: diphtheria toxoid; *B. pertussis* antigens; poliovirus antigens; HBsAg.

Preferably, none of the conjugates is adsorbed to an aluminium salt [2], and more preferably does not include an aluminium salt. Most preferred mixed conjugate components are unadjuvanted. They may, however, contain sugars, such as lactose or, preferably, sucrose.

(21) Adjuvants

In addition to antigenic components, vaccines of the invention will typically include at least one aluminium salt adjuvant. As mentioned above, the vaccines can include both aluminium hydroxide and aluminium phosphate adjuvants. Where both are included, the weight ratio of the two adjuvants is approximately 1:1 e.g. an aluminium hydroxide:aluminium phosphate ratio of about 1.58:1.6.

Although aluminium adjuvants are typically referred to either as "aluminium hydroxide" or as "aluminium phosphate" adjuvants, these are names of convenience, as neither is a precise description of the actual chemical compound which is present [e.g. see chapter 9 of reference 54]. The invention can use any of the "hydroxide" or "phosphate" adjuvants that are in general use as adjuvants.

The adjuvants known as "aluminium hydroxide" are typically aluminium oxyhydroxide salts, which are usually at least partially crystalline. Aluminium oxyhydroxide, which can be represented by the formula AlO(OH), can be distinguished from other aluminium compounds, such as aluminium hydroxide Al(OH)$_3$, by infrared (IR) spectroscopy, in particular by the presence of an adsorption band at 1070 cm$^{-1}$ and a strong shoulder at 3090-3100 cm$^{-1}$ [chapter 9 of ref. 54].

The adjuvants known as "aluminium phosphate" are typically aluminium hydroxyphosphates, often also containing a small amount of sulfate (i.e. aluminium hydroxyphosphate sulfate). They may be obtained by precipitation, and the reaction conditions and concentrations during precipitation influence the degree of substitution of phosphate for hydroxyl in the salt. Hydroxyphosphates generally have a PO$_4$/Al molar ratio between 0.3 and 1.2. Hydroxyphosphates can be distinguished from strict AlPO$_4$ by the presence of hydroxyl groups. For example, an IR spectrum band at 3164 cm$^{-1}$ (e.g. when heated to 200° C.) indicates the presence of structural hydroxyls [ch. 9 of ref. 54].

The adjuvants can take any suitable form (e.g. gel, crystalline, amorphous, etc.).

The PO$_4$/Al$^{3+}$ molar ratio of an aluminium phosphate adjuvant will generally be between 0.3 and 1.2, preferably between 0.8 and 1.2, and more preferably 0.95±0.1. A typical adjuvant is amorphous aluminium hydroxyphosphate with PO$_4$/Al molar ratio between 0.84 and 0.92, included at 0.6 mg Al$^{3+}$/ml. The aluminium phosphate will generally be amorphous, particularly for hydroxyphosphate salts. The aluminium phosphate will generally be particulate. Typical diameters of the particles are in the range 0.5-20 μm (e.g. about 5-10 μm) after any antigen adsorption.

The PZC of aluminium phosphate is inversely related to the degree of substitution of phosphate for hydroxyl, and this degree of substitution can vary depending on reaction conditions and concentration of reactants used for preparing the salt by precipitation. PZC is also altered by changing the concentration of free phosphate ions in solution (more phosphate=more acidic PZC) or by adding a buffer such as a histidine buffer (makes PZC more basic). Aluminium phosphates used according to the invention will generally have a PZC of between 5.0 and 7.0, more preferably between 5.5 and 6.0 e.g. about 5.7.

The aluminium phosphate is preferably used in the form of an aqueous solution to which antigens are added (NB: it is common to refer to aqueous aluminium phosphate as a "solution" although, on a strict physicochemical view, the salt is insoluble and forms a suspension). It is preferred to dilute the aluminium phosphate to the required concentration and to ensure a homogenous solution before the addition of the antigenic components.

The concentration of Al$^{3+}$ prior to addition of antigens is generally between 0 and 10 mg/ml. A preferred concentration is between 2 and 6 mg/ml.

An aluminium phosphate solution used to prepare a vaccine of the invention may contain a buffer (e.g. a phosphate or a histidine buffer), but this is not necessary. The aluminium phosphate solution is preferably sterile and pyrogen-free. The aluminium phosphate solution may include free aqueous phosphate ions e.g. present at a concentration between 1.0 and 20 mM, preferably between 5 and 15 mM, and more preferably about 10 mM. The aluminium phosphate solution may also comprise sodium chloride. The concentration of sodium chloride is preferably in the range of 0.1 to 100 mg/ml (e.g. 0.5-50 mg/ml, 1-20 mg/ml, 2-10 mg/ml) and is more preferably about 3±1 mg/ml. The presence of NaCl facilitates the correct measurement of pH prior to adsorption of antigens.

Where an antigen is described as being "adsorbed" to an adjuvant, it is preferred that at least 50% (by weight) of that antigen is adsorbed e.g. 50%, 60%, 70%, 80%, 90%, 95%, 98% or more. In some embodiments the diphtheria toxoid and tetanus toxoid are both totally adsorbed i.e. none is detectable in supernatant. Total adsorption of HBsAg is also preferred.

(22) Further Components of the Vaccine

As well as containing antigens and adjuvant(s), etc., the combination vaccines of the invention may include further components. These components may have various sources. For example, they may be present in one of the antigenic components that is mixed during the process of the invention or may be added during the process separately from the antigenic components.

To control tonicity of the final vaccine product, it is preferred to include a physiological salt, such as a sodium salt. Sodium chloride (NaCl) is preferred, which may be present in the final vaccine product at between 1 and 20 mg/ml.

Due to the adsorbed nature of antigens, the final vaccine product may be a suspension with a cloudy appearance. This appearance means that microbial contamination is not readily visible, and so the vaccine preferably contains an antimicrobial agent. This is particularly important when the vaccine is packaged in multidose containers. Preferred antimicrobials for inclusion are 2-phenoxyethanol and thimerosal. It is preferred, however, not to use mercurial preservatives (e.g. thimerosal) during the process of the invention. However, the presence of trace amounts may be unavoidable if an antigen used during the process (e.g. HBsAg) has previously been treated with such a preservative. For safety, however, it is preferred that the final vaccine product contains less than about 25 ng/ml mercury. More preferably, the final vaccine product contains no detectable thimerosal. This will generally be achieved by removing the mercurial preservative from an antigen preparation prior to its addition in the process of the invention or by avoiding the use of thimerosal during the preparation of individual antigenic components.

As well as substances such as thimerosal, other residual components from the individual antigens may also be present in trace amounts in the final vaccine produced by the process of the invention. For example, if formaldehyde is used to prepare the toxoids of diphtheria, tetanus and pertussis then the final vaccine product may retain trace amounts of formaldehyde (e.g. less than 10 μg/ml, preferably <5 μg/ml). Free amino acids (e.g. alanine, arginine, aspartate, cysteine and/or cystine, glutamate, glutamine, glycine, histidine, proline and/or hydroxyproline, isoleucine, leucine, lysine, methionine, phenylalanine, serine, threonine, tryptophan, tyrosine and/or valine), vitamins (e.g. choline, ascorbate, etc.), disodium phosphate, monopotassium phosphate, calcium, glucose, adenine sulfate, phenol red, sodium acetate, potassium chloride, etc. may be retained in the final vaccine at ≤100 μg/ml of each (e.g. ≤50 μg/ml, ≤10 μg/ml). A further possible component of the final vaccine which originates in the antigen preparations arises from less-than-total purification of antigens. Small amounts of *B. pertussis, C. diphtheriae, C. tetani* and *S. cerevisiae* proteins and/or genomic DNA may therefore be present. To minimize the amounts of these residual components, antigen preparations are preferably treated to remove them prior to the antigens being used in the process of the invention.

Where aluminium salts are present within the final vaccine, the total amount of aluminium, expressed in terms of $Al^{3+}$, is preferably ≤2 mg/ml (e.g. between 1.2-1.5 mg/ml, or about 1.4 mg/ml; or between 0.4 and 0.8 mg/ml, or about 0.6 mg/ml).

During the process of the invention, dilution of components to give desired final concentrations will usually be performed with WFI (water for injection).

To prevent interference between antigens, particularly conjugate antigens, it is possible to include a polyanionic polymer, such as poly-L-glutamic acid [55].

(23) Packaging of the Combination Vaccine

In typical use, the process of the invention will be used to provide bulk combination vaccine which is suitable for packaging, and then for distribution and administration. Concentrations mentioned above are typically concentrations in final packaged vaccine, and so concentrations in bulk vaccine may be higher (e.g. to be reduced to final concentrations by dilution).

The process of the invention may therefore comprise the further step of packaging the vaccine into containers for use. Suitable containers include vials and disposable syringes (preferably sterile ones).

Where the vaccine is packaged into vials, these are preferably made of glass or of a plastic material. The vial is preferably sterilized before vaccine is added to it. To avoid problems with latex-sensitive patients, vials can be sealed with a latex-free stopper. The vial may include a single dose of vaccine, or it may include more than one dose (a 'multidose' vial) e.g. 10 doses. When using a multidose vial, each dose should be withdrawn with a sterile needle and syringe under strict aseptic conditions, taking care to avoid contaminating the vial contents. Preferred vials are made of colorless glass.

Where the vaccine is packaged into a syringe, the syringe will not normally have a needle attached to it, although a separate needle may be supplied with the syringe for assembly and use. Safety needles are preferred. 1-inch 23-gauge, 1-inch 25-gauge and ⅝-inch 25-gauge needles are typical. Syringes may be provided with peel-off labels on which the lot number and expiration date of the contents may be printed, to facilitate record keeping. The plunger in the syringe preferably has a stopper to prevent the plunger from being accidentally removed during aspiration. The syringes may have a latex rubber cap and/or plunger. Disposable syringes contain a single dose of vaccine. The syringe will generally have a tip cap to seal the tip prior to attachment of a needle, and the tip cap is preferably made of butyl rubber. If the syringe and needle are packaged separately then the needle is preferable fitted with a butyl rubber shield. Grey butyl rubber is preferred. Preferred syringes are those marketed under the trade name "Tip-Lok"™.

Where a glass container (e.g. a syringe or a vial) is used, then it is preferred to use a container made from a borosilicate glass rather than from a soda lime glass.

When contained separately, conjugate antigens will typically be freeze-dried (lyophilized) in a separate container, such that the packaged vaccine will contain at least two separate containers. Prior to administration to a patient, the freeze-dried material will be reconstituted and diluted with the liquid from the other container. Typically, therefore, the conjugate container will be a vial and the other container will contain a liquid within a vial or a pre-filled syringe. The liquid contents of the second container will be transferred into the vial containing the freeze-dried conjugate antigen powder, thereby reconstituting the conjugate antigens for administration to a patient.

The container for lyophilised conjugates is preferably a vial which has a cap (e.g. a Luer lock) adapted such that a pre-filled syringe can be inserted into the cap, the contents of the syringe can be expelled into the vial to reconstitute the freeze-dried material therein, and the contents of the vial can be removed back into the syringe. After removal of the syringe from the vial, a needle can then be attached and the vaccine can be administered to a patient. The cap is preferably located inside a seal or cover, such that the seal or cover has to be removed before the cap can be accessed.

The combination vaccine of the invention is preferably administered to patients in 0.5 ml doses. The process of the invention may therefore comprise the step of extracting and packaging a 0.5 ml sample of the bulk vaccine into a container. For multidose situations, multiple dose amounts will be extracted and packaged together in a single container. Where a vaccine is presented as a kit with a lyophilised component then the final dose after reconstitution is preferably 0.5 ml. References to 0.5 ml doses herein should be taken to mean 0.5 ml±0.05 ml.

The container in which the vaccine is packaged will usually then be enclosed within a box for distribution e.g. inside a cardboard box, and the box will be labeled with details of the vaccine e.g. its trade name, a list of the antigens in the vaccine (e.g. 'Diphtheria, tetanus, inactivated whole cell pertussis and hepatitis B recombinant, adsorbed vaccine', etc.), the presentation container (e.g. 'Disposable Prefilled Tip-Lok Syringes' or '10×0.5 ml Single-Dose Vials'), its dose (e.g. 'each containing one 0.5 ml dose'), warnings (e.g. 'For Pediatric Use Only'), an expiration date, etc. Each box might contain more than one packaged vaccine e.g. five or ten packaged vaccines (particularly for vials). If the vaccine is contained in a syringe then the package may show a picture of the syringe.

The vaccine may be packaged together (e.g. in the same box) with a leaflet including details of the vaccine e.g. instructions for administration, details of the antigens within the vaccine, etc. The instructions may also contain warnings e.g. to keep a solution of adrenaline readily available in case of anaphylactic reaction following vaccination, etc.

The packaged vaccine materials are preferably sterile.

The packaged vaccine materials are preferably non-pyrogenic e.g. containing <1 EU (endotoxin unit, a standard measure) per dose, and preferably <0.1 EU per dose.

The packaged vaccine materials are preferably gluten free.

The pH of any aqueous packaged vaccine materials is preferably between 6 and 8 e.g. between 6.5 and 7.5. The process of the invention may therefore include a step of adjusting the pH of the bulk vaccine prior to packaging.

Any aqueous material within the packaged vaccine is preferably a turbid white suspension.

The packaged vaccine is preferably stored at between 2° C. and 8° C. It should not be frozen.

(24) Administration of the Vaccine

The final combination vaccines of the invention are suitable for administration to humans, and in particular to children. A typical dosage schedule for the vaccine, or order to have full efficacy, will involve administering more than one dose in a primary immunization schedule. A typical primary schedule will involve three doses, given at intervals of about 6 to 8 weeks, with the first dose being given to a child aged between 6 and 9 weeks of age. A 3-dose primary schedule at 6, 10 and 14 weeks of age is preferred, and this may be followed up with a fourth dose at 18 months.

The vaccine may also be used to complete the primary immunization schedule of a different vaccine.

The invention provides a method for raising an immune response in a patient, comprising administering a composition of the invention to the patient.

The invention also provides a composition of the invention, for use in medicine.

The invention also provides the use of (i) a diphtheria toxoid, (ii) a tetanus toxoid, (iii) a cellular pertussis antigen, (iv) a hepatitis B virus surface antigen, (v) a *Haemophilus influenzae* type b capsular saccharide conjugated to a carrier protein, (vi) at least one *Neisseria meningitidis* capsular saccharide conjugated to a carrier protein, in the manufacture of a medicament for immunising a patient.

The invention also provides the use of (i) a diphtheria toxoid, (ii) a tetanus toxoid, (iii) a cellular pertussis antigen, (iv) a hepatitis B virus surface antigen, in the manufacture of a medicament for immunising a patient, wherein the medicament is used to reconstitute a conjugate mixture.

The invention also provides the use of (i) a *Haemophilus influenzae* type b capsular saccharide conjugated to a carrier protein and (ii) at least one *Neisseria meningitidis* capsular saccharide conjugated to a carrier protein, in the manufacture of a medicament for immunising a patient, wherein the medicament is lyophilised and is administered after reconstitution by an aqueous vaccine comprising at least one further antigen.

Further specific features of various medicaments are given above. Preferred medicaments are vaccines.

Medicaments will generally be administered directly to a patient. Direct delivery may be accomplished by parenteral injection (e.g. intravenously, subcutaneously, intraperitoneally, intramuscularly, or to the interstitial space of a tissue), or by rectal, oral, vaginal, topical, transdermal, intranasal, ocular, aural, pulmonary or other mucosal administration. In general, however, they are administered by intramuscular injection. Preferred sites for injection are the anterolateral thigh or the deltoid muscle of the upper arm.

These uses, methods and medicaments are preferably for immunisation against the pathogens stated above. The patient is preferably a human, and may be a child (e.g. a toddler or infant), a teenager or an adult, but will generally be a child. Preferred patients are aged between 0-36 months e.g. between 0-24 months, between 0-12 months, or between 0-6 months.

Methods for checking the efficacy of the separate antigens are known in the art.

Vaccines of the invention may be administered at substantially the same time as an oral polio vaccine, such as a trivalent oral polio vaccine e.g. containing Type 1 poliovirus, Type 2 poliovirus and Type 3 poliovirus. A child receiving the vaccine of the invention for the first time may have previously received oral polio vaccine and/or *Bacillus* Calmette-Guérin (BCG) vaccine.

Thus preferred patient groups for immunisation include, but are not limited to: (a) children who have previously received oral polio vaccine; (b) children who have previously received BCG vaccine; (c) children who have previously received both oral polio and BCG vaccine; (d) children in group (a), (b) or (c) who have not previously received any of D, T, Pw, HBsAg, Hib conjugates and at least one meningococcal conjugate; and (e) children who have previously received oral polio vaccine, BCG, D, T, Pw, HBsAg, Hib conjugate and at least one meningococcal conjugate. These children may be in any of the age groups specified above e.g. 0-36, 0-24, 0-12 or 0-6 months.

Thus the invention provides the use of (i) a diphtheria toxoid, (ii) a tetanus toxoid, (iii) a cellular pertussis antigen, (iv) a hepatitis B virus surface antigen, (v) a *Haemophilus influenzae* type b capsular saccharide conjugated to a carrier protein, (vi) at least one *Neisseria meningitidis* capsular saccharide conjugated to a carrier protein, in the manufacture of a medicament for immunising a patient in one of said groups (a) to (e).

If the vaccine of the invention contains an aluminium-based adjuvant, settling of components may occur during storage. The vaccine should therefore be shaken prior to administration to a patient. The shaken vaccine will be a turbid white suspension.

General

The term "comprising" can mean "including" as well as "consisting" e.g. a composition "comprising" X may consist exclusively of X or may include something additional e.g. X+Y.

The word "substantially" does not exclude "completely" e.g. a composition which is "substantially free" from Y may be completely free from Y. Where necessary, the word "substantially" may be omitted from the definition of the invention.

The term "about" in relation to a numerical value x means, for example, x±10%.

General information on conjugation techniques can be found in reference 39.

BRIEF DESCRIPTION OF THE DRAWINGS

FIGS. 1A-1D shows western blot results for HBsAg stability in a composition. In FIG. 1A, the lanes are: (1) Laemmli sample buffer (LSB); (2) MW markers; (3-5) 1 µg of three separate control HBsAg preparations; (6-8) supernatant of three separate pentavalent lots; (9-10) LSB. In FIG. 1B, the lanes are: (1) MW markers; (2-4) 1 µg of three separate control HBsAg preparations; (5-7) supernatant of three separate pentavalent lots, stored for 2 weeks at 2-8° C.; (8-10) supernatant of three separate pentavalent lots, stored for 2 weeks at 36-38° C. In FIG. 1C, the lanes are: (1) MW markers; (2-4) 1 µg of three separate control HBsAg preparations; (5-7) supernatant of three separate pentavalent lots, stored for 4 weeks at 2-8° C.; (8-10) supernatant of three separate pentavalent lots, stored for 4 weeks at 36-38° C. In FIG. 1B, the lanes are: (1) MW markers; (2-4) 1 µg of three separate control HBsAg preparations; (5-7) supernatant of three separate pentavalent lots, stored for 6 months at 2-8° C.

FIG. 2 shows the variation of pH over time for a pentavalent composition. FIG. 2A shows variation of pH in the pentavalent vaccine over 6 months for three lots stored at 2-8° C. FIG. 2B shows variation of pH over 4 weeks for three lots stored at 36-38° C.

FIG. 3 shows western blot results for HBsAg stability in an octavalent composition. In FIGS. 3A and 3B: lane 1 contains MW markers; lane 2 contains a HBsAg control at 1 µg/ml; lane 3 contains the supernatant of the octavalent composition. In FIG. 3B: lane 4 contains LSB; lane 5 contains the same control as lane 2; lane 6 contains a DOC/TCA extract.

MODES FOR CARRYING OUT THE INVENTION

Octavalent D-T-Pw-HBsAg-Hib-MenC-MenW135-MenY Vaccine

Figure 1C:
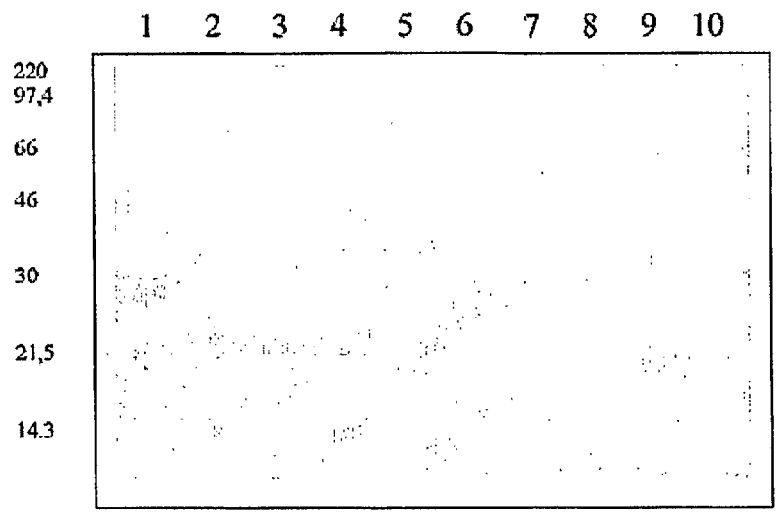

Yeast-expressed HBsAg, diphtheria toxoid, tetanus toxoid and whole-cell pertussis antigens were added to a suspension of an aluminium salt adjuvant. The pH of the mixture was adjusted, and then a Hib-CRM197 conjugate was added, such that it did not become adsorbed to the aluminium adjuvant. This process gave a pentavalent vaccine with the following composition:

| Component | Concentration |
|---|---|
| Diphtheria toxoid | 15 Lf/ml |
| Tetanus toxoid | 6.5 Lf/ml |
| Whole cell pertussis antigen | 30 OU/ml |
| HBsAg | 20 μg/ml |
| CRM-Hib | 20 μg/ml (as saccharide) |
| $Al^{3+}$ | 0.6 mg/ml |
| NaCl | 9 mg/ml |

In further work, separate meningococcal-CRM197 conjugates from each of serogroups C, W135 and Y were added after the CRM-Hib component in order to give an octavalent vaccine:

| Component | Concentration |
|---|---|
| Diphtheria toxoid | 15 Lf/ml |
| Tetanus toxoid | 6.5 Lf/ml |
| Whole cell pertussis antigen | 30 OU/ml |
| HBsAg | 20 μg/ml |
| CRM-Hib | 20 μg/ml |
| CRM-MenC | 20 μg/ml |
| CRM-MenW135 | 20 μg/ml |
| CRM-MenY | 20 μg/ml |
| $Al^{3+}$ | 0.6 mg/ml |
| NaCl | 9 mg/ml |

An important parameter for vaccine stability and efficacy is the percentage of hydrolysis of Hib conjugate, the clinical limit being 25% free saccharide (reference 56 reports that 20% did not affect clinical immunogenicity). This parameter was measured in the pentavalent vaccine by HPAEC-PAD, which permits direct quantification of non-conjugated carbohydrates at picomolar levels with minimal separation and clean-up. Analysis focused on the amount of free saccharide. Saccharide was assayed for:
  (a) the total amount in μg/ml
  (b) the amount in the supernatant (i.e. unadsorbed) in μg/ml
  (c) the amount which is free (hydrolysis of the CRM197-Hib conjugate) in μg/ml Value (c) was expressed either as (d) a percentage of (b) or as (e) a percentage of the theoretical total saccharide concentration (20 μg/ml). Results were as follows:

| Lot | Time | (a) | (b) | (c) | (d) | (e) |
|---|---|---|---|---|---|---|
| 1 | 0 | 23.47 | 21.30 | 1.26 | 5.3% | 6.3% |
|  | 2 weeks, 2-8° C. | 18.39 | 19.12 | 1.04 | 5.7% | 5.2% |
|  | 2 weeks, 36-38° C. | 19.84 | 17.18 | 1.36 | 6.8% | 6.8% |
|  | 4 weeks, 2-8° C. | 22.51 | 20.57 | 1.49 | 6.5% | 7.3.% |
|  | 4 weeks, 36-38° C. | 21.30 | 18.15 | 2.47 | 11.6% | 12.3% |
| 2 | 0 | 23.23 | 22.26 | 0.70 | 3.0% | 3.5% |
|  | 2 weeks, 2-8° C. | 21.06 | 19.36 | 0.65 | 3.1% | 3.3% |
|  | 2 weeks, 36-38° C. | 21.54 | 16.70 | 1.19 | 5.5% | 5.9% |
|  | 4 weeks, 2-8° C. | 23.72 | 19.84 | 0.87 | 3.7% | 4.4% |
|  | 4 weeks, 36-38° C. | 23.72 | 18.63 | 1.91 | 8.1% | 9.6% |
| 3 | 0 | 24.20 | 23.23 | 0.80 | 3.3% | 4.0% |
|  | 2 weeks, 2-8° C. | 20.09 | 17.67 | 0.80 | 4.0% | 4.0% |
|  | 2 weeks, 36-38° C. | 18.15 | 17.18 | 1.14 | 6.3% | 5.7% |
|  | 4 weeks, 2-8° C. | 22.99 | 23.23 | 0.94 | 4.1% | 4.7% |
|  | 4 weeks, 36-38° C. | 22.26 | 18.39 | 1.94 | 8.7% | 9.7% |

A maximum of 25% free saccharide is clinically acceptable. All values were below this threshold, and were below 6.5% for up to 4 weeks at 2-8° C. Under thermal stress conditions (4 weeks at 36-38° C.) a higher level was seen, but still well below the 25% value, with the maximum being 11.6% for lot 1. Earlier work on multivalent Hib vaccines has shown that one month of storage at 36-38° C. gives more CRM-Hib hydrolysis than two years of storage at 2-8° C. Acceptable hydrolysis can thus be expected over at least a 2 year time-scale under normal storage conditions.

HPAEC-PAD analysis of free saccharide was also carried out after 6 months at 2-8° C. The data were as follows:

| Lot | (c) | (d) | (e) |
|---|---|---|---|
| 1 | 1.65 | 9.8% | 8.3% |
| 2 | 1.09 | 5.8% | 5.5% |
| 3 | 1.16 | 6.6% | 5.8% |

Thus there is only a small increase in the percentage of free saccharide at 6 months compared to 4 weeks, with values still well below the 25% value. CRM197-Hib is thus very stable in the three formulations.

FIG. 2A shows variation of pH in the pentavalent vaccine over 6 months for three lots stored at 2-8° C. FIG. 2B shows variation of pH over 4 weeks for three lots stored at 36-38° C. At 2-8° C. pH was stable over 6 months, while under thermal stress conditions there was a slight drop of 0.1 pH unit after 2 weeks and a further slight drop after 4 weeks. Even so, all pH values remained within the accepted range of 6.0-7.0.

Osmolarity of all three pentavalent lots was between 312 and 315 mOsm/Kg, centrally within the accepted range of 240-360 mOsm/Kg for injectable vaccines.

Evaluation of the potency and immunogenicity of antigens is important in order to assess the efficacy of a combination vaccine. The potency of Diphtheria, Tetanus and Pertussis antigens in the pentavalent vaccine was evaluated and the immunogenicity of both CRM-Hib and HBsAg was tested. ELISA analysis was carried out to evaluate the level of specific antibodies after immunisation. Immunogenicity of HBsAg was performed using a mouse model and a different immunisation schedule with respect to that used for the HBV potency.

DTP potency values were as follows:

|  | D | T | P |
|---|---|---|---|
| Lot 1 | 41 | 161 | 4 |
| Lot 2 | 39 | 138 | 5 |
| Lot 3 | 39 | 143 | 6 |

For each of these three antigens the potency test results are all significantly above accepted lower limits and these results indicate good efficacy for these three antigens.

For assessing HBsAg immunogenicity, groups of 10 CD1 mice received the pentavalent vaccine by subcutaneous injection (0.5 ml, diluted 1:4 in saline) at days 0 and 14. The mice were bled on day 21 and HBsAg-specific antibodies were assessed by ELISA using either (a) the "Enzygnost Anti-HBs II" test (Dade Behring) or (b) the "Ausab EIA" test (Abbott). These ELISA tests have different formats and different sensitivities to HBsAg. Geometric Mean Titre values are thus not comparable between the two tests. However, within the scope of each test the GMT values for the sera were optimal. Results were as follows:

|  | Enzygnost | | Ausab EIA | |
|---|---|---|---|---|
|  | GMT | % responders | GMT | % responders |
| Lot 1 | 1008 | 100 | 192 | 100 |
| Lot 2 | 1518 | 100 | 194 | 100 |

-continued

|  | Enzygnost | | Ausab EIA | |
|---|---|---|---|---|
|  | GMT | % responders | GMT | % responders |
| Lot 3 | 461 | 90 | 127 | 100 |
| Adjuvant only | 2 | 0 | 2 | 0 |

All the GMT values obtained performing this kind of mouse immunogenicity assay are higher than the values reported in the literature. The percentage of responders is consistently high for both antigens at an optimum level of ~100%.

For assessing Hib immunogenicity, groups of 8 CD1 mice received the pentavalent vaccine by subcutaneous injection (0.5 ml, diluted 1:4 in saline) at days 0, 10 and 20. The mice were bled on day 34 and Hib-specific antibodies were assessed by ELISA. Results were as follows:

|  | % responders |
|---|---|
| Lot 1 | 100 |
| Lot 2 | 100 |
| Lot 3 | 100 |
| Adjuvant only | 0 |

Adsorption of HBsAg to the aluminium adjuvant is an important factor for vaccine immunogenicity, and this parameter was measured by immunoblot. The immunoblot procedure followed was essentially as follows: a 1 ml volume of vaccine supernatant was DOC/TCA precipitated and denatured with LSB and then loaded on a 12% acrylamide SDS-PAGE; 1 µg of each lot of HBsAg was loaded as control; a goat anti-HBsAg antibody preparation was used as primary antibody (diluted 1:1000) and an anti-goat POD conjugate (diluted 1:2500) was used as secondary antibody.

Results for the pentavalent vaccine are shown in FIGS. 1A-1D. Lanes 6-8 of FIG. 1A show that there is no detectable soluble HBsAg in the composition at time zero, and lanes 5-10 of FIGS. 1B & 1C confirm that this remains true after 2 weeks and 4 weeks of storage at 2-8° C. or 36-38° C. In three different lots, ~99% of HBsAg remains adsorbed onto the adjuvant under these various conditions.

Figure 1D:
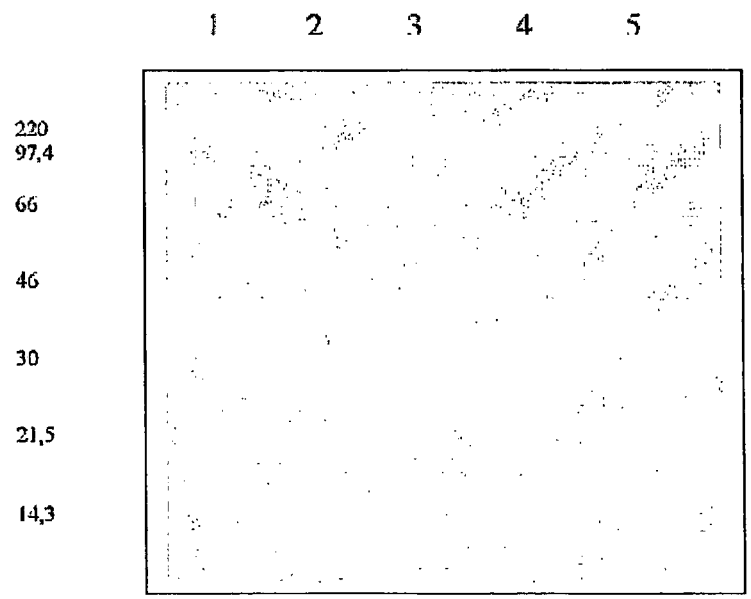

An additional stability assay was performed after 6 months of storage at 2-8° C. (FIG. 1D). Adsorption remained at ~99% for each of the three lots.

The positive controls used in FIGS. 1A-1D contained 1 µg HBsAg. A single band corresponding to the S peptide (24 kDa) was seen, plus a band characteristic of aggregates (~45 kDa). Pre-S2 was not seen.

The octavalent vaccine was also tested for HBsAg adsorption in a similar way. A 1 ml sample was centrifuged at 3500 rpm for 10 minutes. The supernatant was removed to a fresh tube and precipitated with DOC/TCA. The pellet was resuspended in 200 µl extraction buffer, boiled for 5 minutes and centrifuged at 1300 rpm for 10 minutes. 20 µl of this extract and the supernatant precipitated with DOC/TCA were loaded on 12% SDS-PAGE for Western-Blot.

FIG. 3A shows the octavalent vaccine at time zero, and FIG. 3B shows the vaccine after 8 months of storage at 2-8° C. The absence of any significant staining in lanes 3 & 6 of FIG. 3B (certainly less staining than seen with 1 µg of HBsAg in control lanes 2 & 5) shows that HBsAg adsorption remains stable over this storage period.

Heptavalent D-T-Pw-HBsAg-Hib-MenA-MenC Vaccine

Five antigenic components are collected as follows:

A TRIVALENT D-T-Pw COMPONENT: A D-T-Pw component was prepared that includes diphtheria toxoid adsorbed to an aluminium hydroxide adjuvant, tetanus toxoid also adsorbed to an aluminium hydroxide adjuvant, and whole-cell pertussis antigens with aluminium phosphate. This component contains thimerosal, but contains no 2-phenoxyethanol.

A HBsAg COMPONENT: HBsAg is expressed and purified from a recombinant S. cerevisiae. The purified protein is adsorbed onto an aluminium phosphate antigen [17].

A Hib CONJUGATE COMPONENT: Hib polysaccharide is prepared from Hib, strain 20752 and after activation with cyanogen bromide and derivatisation with an adipic hydrazide spacer is covalently coupled to a tetanus toxoid via carbodiimide condensation, at a saccharide:carrier weight ratio of about 1:3. After the reaction involving EDAC, EDU levels are measured.

A MenA CONJUGATE COMPONENT: Capsular saccharide from serogroup A meningococcus is purified and covalently conjugated to H. influenzae protein D using the CDAP technique. After the reaction involving CDAP, residual DMAP content is measured, and retention of OAc groups at C-3 is confirmed. A conjugate using a tetanus toxoid carrier is also prepared, also by CDAP conjugation.

A MenC CONJUGATE COMPONENT: Capsular saccharide from an OAc+ serogroup C meningococcus is purified and covalently conjugated to H. influenzae protein D using the CDAP technique. After the reaction involving CDAP, residual DMAP content is measured. Conjugates are also prepared from an OAc− strain. A conjugate using a tetanus toxoid carrier is also prepared, also by CDAP conjugation.

The D-T-Pw component is mixed with the HBsAg component, and this tetravalent mixture is packaged in aqueous form into a stoppered vial. The HBsAg level is 10 µg/dose.

The three conjugates are mixed and lyophilised as described in reference 2. The lyophilised powder is packaged in a stoppered vial. Each conjugate is present at 5 µg/dose. A mixture with double this dose of each conjugate is also prepared. The conjugate mixture is adjuvant-free.

The two vials are packaged together in a box.

For patient administration, the aqueous D-T-Pw-HBsAg material is withdrawn into a syringe, and is introduced into the lyophilised conjugate vial. After the lyophilised material is reactivated, it is withdrawn back into the syringe, ready for administration to patients.

Infants are given a 3-dose primary vaccination at 6, 10 and 14 weeks, administered by intramuscular injection. For comparison, 140 infants receive GSK's TRITANRIX-HepB/Hib vaccine. The vaccine shows excellent immunogenicity.

In a follow-up trial, infants receive the 7-valent vaccine at 6, 10 and 14 weeks. Control patients receive either TRITANRIX-HepB/Hib or TRITANRIX-HepB/Hib plus the MENINGITEC vaccine. Serum antibody levels are measured prior to and one month after this primary vaccination course. Solicited local and general adverse events are recorded for eight days and unsolicited adverse events for 30 days following each vaccine dose. Following the primary course, 99%-100% of subjects receiving the 7-valent vaccine reach an anti-PRP level of ≥0.15 µg/ml compared to 100% in the TRITANRIX-HepB/Hib control group. 99-100% of subjects receiving the 7-valent vaccine have a SBA-MenC titer ≥1:8 (vs. 100% of subjects receiving Meningitec). At least 97.7% of subjects receiving the 7-valent vaccine have a SBA-MenA titer ≥1:8 (vs. <10% of subjects receiving Meningitec). Seroprotection levels against diphtheria, tetanus and hepatitis B antigens and the anti-*B. pertussis* toxoid concentration induced by the 7-valent vaccines are high and similar to the control vaccines. The incidence of clinically relevant solicited/unsolicited adverse events was low and equally distributed among all groups. No serious adverse event related to vaccination was reported. The 7-valent vaccine exhibits excellent immunogenicity and a good safety profile, suggesting that it is a suitable combination vaccine for primary vaccination of infants living in endemic regions for MenA and MenC.

In a further study, the immune memory and antibody persistence to Hib, MenA and MenC components of the vaccine in infants aged 10 months is evaluated. Antibody persistence and immune memory to Hib, MenA and MenC in infants primed with the 7-valent vaccine is excellent: 10 μg of each conjugate elicits high levels of corresponding antibodies, demonstrating that priming by the conjugate vaccine is adequate since it is higher than the response in unprimed young children (for MenA and MenC) and similar to Hiberix™ (for Hib).

It will be understood that the invention has been described by way of example only and modifications may be made whilst remaining within the scope and spirit of the invention.

REFERENCES

The Contents of which are Hereby Incorporated by Reference

[1] *Vaccines*. (eds. Plotkin & Orenstein). 4th edition, 2004, ISBN: 0-7216-9688-0.
[2] WO02/00249.
[3] Gatchalian et al. (2004) Abstract SI-68 of *Fourteenth International Pathogenic Neisseria Conference*.
[4] Gatchalian et al. (2004) Abstract SI-69 of *Fourteenth International Pathogenic Neisseria Conference*.
[5] WO96/40242.
[6] U.S. Pat. No. 5,693,326.
[7] Arakere & Frasch (1991) *Infect. Immun.* 59:4349-4356.
[8] Michon et al. (2000) *Dev. Biol.* 103:151-160.
[9] Rubinstein & Stein (1998) *J. Immunol.* 141:4357-4362.
[10] Campbell et al. (2002) *Pediatr Infect Dis J* 21:822-826.
[11] Guimaraes et al. (2002) *Int J Infect Dis* 6:113-117.
[12] Lagos et al. (1998) *Lancet* 351:1472-1476.
[13] Fernandez et al. (2000) *Am J Trop Med Hyg* 62:485-490.
[14] Nicol et al. (2002) *Pediatr Infect Dis J* 21:138-141.
[15] WO02/05846.
[16] Korean patent 92-9729 (1992-0009729).
[17] WO93/24148.
[18] WO03/066094.
[19] Beuvery et al. (1986) *Dev Biol Stand* 63:117-28.
[20] Sesardic et al. (2001) *Biologicals* 29:107-22.
[21] NIBSC code: 98/560.
[22] Module 1 of WHO's *The immunological basis for immunization series* (Galazka).
[23] NIBSC code: 69/017.
[24] NIBSC code: DIFT.
[25] Sesardic et al. (2002) *Biologicals* 30:49-68.
[26] NIBSC code: 98/552.
[27] NIBSC code: TEFT.
[28] NIBSC code: 66/303.
[29] Vanlandschoot et al. (2005) *J Gen Virol* 86:323-31.
[30] Ramsay et al. (2001) *Lancet* 357(9251): 195-196.
[31] Lindberg (1999) *Vaccine* 17 Suppl 2:S28-36.
[32] Buttery & Moxon (2000) *J R Coll Physicians Lond* 34:163-168.
[33] Ahmad & Chapnick (1999) *Infect Dis Clin North Ami* 13:113-133, vii.
[34] Goldblatt (1998) *J. Med. Microbiol.* 47:563-567.
[35] European patent 0477508.
[36] U.S. Pat. No. 5,306,492.
[37] WO98/42721.
[38] *Conjugate Vaccines* (eds. Cruse et al.) ISBN 3805549326, particularly vol. 10:48-114.
[39] Hermanson (1996) *Bioconjugate Techniques* ISBN: 0123423368 or 012342335X.
[40] Armand et al. (1982) *J. Biol. Stand.* 10:335-339.
[41] Cadoz et al. (1985) *Vaccine* 3:340-342.
[42] Jones (2001) *Curr Opin Investig Drugs* 2:47-49.
[43] Costantino et al. (1992) *Vaccine* 10:691-8.
[44] Lieberman et al. (1996) *JAMA* 275:1499-503.
[45] WO02/058737.
[46] WO03/007985.
[47] Rennels et al. (2002) *Pediatr Infect Dis J* 21:978-979.
[48] Campbell et al. (2002) *J Infect Dis* 186:1848-1851.
[49] WO91/18926 and U.S. Pat. Nos. 5,858,677, 5,888,517, 5,989,828, 6,025,484 & 6,139,846
[50] Janson et al. (1991) *Infect Immun* 59:119-25.
[51] WO00/56360.
[52] WO99/42130.
[53] *W.H.O. Tech. Rep. Ser.* 594:51, 1976.
[54] *Vaccine Design: The Subunit and Adjuvant Approach* (eds. Powell & Newman) Plenum Press 1995 (ISBN 0-306-44867-X).
[55] WO2004/110480.
[56] Sturgess et al. (1999) *Vaccine* 17:1169-1178.

The invention claimed is:

1. A vaccine composition comprising:
(i) a diphtheria toxoid, 'D';
(ii) a tetanus toxoid, 'T';
(iii) a cellular pertussis antigen, 'wP';
(iv) a hepatitis B virus surface antigen, 'HBsAg';
(v) a *Haemophilus influenzae* type b ('Hib') capsular saccharide conjugated to a carrier protein; and
(vi) at least one *Neisseria meningitidis* capsular saccharide conjugated to a carrier protein, wherein the at least one *Neisseria meningitidis* capsular saccharide comprises an O-acetyl (OAc+) *Neisseria meningitidis* serogroup C capsular saccharide, wherein the *H. influenzae* type b capsular saccharide and the *N. meningitidis* capsular saccharide(s) are each conjugated to a tetanus toxoid carrier protein, or the *N. meningitidis* capsular saccharide(s) is conjugated to a tetanus toxoid, diphtheria toxoid, or CRM197 carrier protein, and wherein the conjugate of component (v) has a weight excess of carrier, and wherein the weight ratio of saccharide to carrier is between 1:2 and 1:4.

2. The vaccine of claim 1, wherein component (vi) includes saccharides from serogroups A and C of *N. meningitidis*.

3. The vaccine of claim 1, wherein the conjugate of component (v) is obtainable by a process comprising the steps of: (a) activating a *Haemophilus influenza* type b capsular saccharide with cyanogen bromide, to give a cyanate ester; (b) adding an adipic hydrazide spacer to the cyanate ester, to give an activated saccharide; and (c) coupling the activated saccharide to a carrier protein by carbodiimide condensation.

4. The vaccine of claim 1, wherein the conjugate of component (v) includes a linker with the following structure:

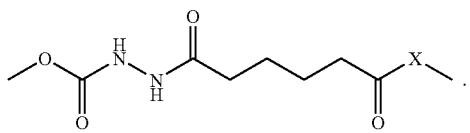

5. The vaccine of claim 1, wherein the conjugate(s) of component (vi) is/are obtainable by a process comprising the steps of: (a) cyanylating a meningococcal capsular saccharide to give a cyanate ester; and (b) coupling the cyanate ester directly to a protein carrier.

6. The vaccine of claim 5, further comprising a meningococcal capsular saccharide from serogroup A.

7. The vaccine of claim 6, wherein the meningococcal serogroup A capsular saccharide has at least 80% of its mannosamine residues O-acetylated at the C-3 position.

8. The vaccine of claim 1, wherein the vaccine includes between 8 µg/ml and 12 µg/ml of the conjugate of component (v).

9. The vaccine of claim 1, wherein a unit dose of the vaccine includes between 8 µg/ml and 12 µg/ml of the conjugate of component (v).

10. The vaccine of claim 1, wherein the vaccine includes between 8 µg/ml and 12 µg/ml of the conjugate(s) of component (vi).

11. The vaccine of claim 1, wherein a unit dose of the vaccine includes between 8 µg/ml and 12 µg/ml of the conjugate(s) of component (vi).

12. The vaccine of claim 1, wherein the vaccine includes both an aluminium phosphate adjuvant and an aluminium hydroxide adjuvant.

13. The vaccine of claim 1, wherein the HBsAg is absorbed to an aluminium phosphate adjuvant.

14. The vaccine of claim 1, wherein the diphtheria toxoid is absorbed to an aluminium hydroxide adjuvant.

15. The vaccine of claim 1, wherein the tetanus toxoid is absorbed to an aluminium hydroxide adjuvant.

16. The vaccine of claim 1, wherein the vaccine includes a mercurial preservative and a 2-phenoxyethanol preservative.

17. The vaccine of claim 1, wherein the ratio of diphtheria toxoid to tetanus toxoid is between 2:1 and 3:1, measured in Lf units.

18. The vaccine of claim 1, wherein the HBsAg is non-glycosylated and is in the form of particles that include a lipid matrix comprising phospholipids and phosphatidylinositol.

19. The vaccine of claim 1, wherein the HBsAg is from HBv subtype adw2.

20. The vaccine of claim 1, wherein the vaccine for administration to patients in a 0.5 ml dose.

21. The vaccine composition of claim 1, wherein the *Neisseria meningitidis* serogroup C capsular saccharide conjugated to the carrier protein is not adsorbed to an aluminum salt.

* * * * *